(12) United States Patent
Lee et al.

(10) Patent No.: US 7,166,641 B2
(45) Date of Patent: Jan. 23, 2007

(54) PHARMACEUTICALLY ACCEPTABLE SALTS CONTAINING LOCAL ANESTHETIC AND ANTI-INFLAMMATORY ACTIVITIES AND METHODS FOR PREPARING THE SAME

(75) Inventors: Fang-Yu Lee, Taichung (TW); Shan-Chiung Chen, Fengyuan (TW); Bin-Ken Chen, Taichung (TW); Chiung-Ju Tsai, Miaoli (TW); Yen-Ling Yi, Taichung (TW)

(73) Assignee: Yung Shin Pharmaceutical Industrial Co., Ltd. (TW)

( * ) Notice: Subject to any disclaimer, the term of this patent is extended or adjusted under 35 U.S.C. 154(b) by 144 days.

(21) Appl. No.: 10/262,098

(22) Filed: Oct. 2, 2002

(65) Prior Publication Data

US 2004/0068007 A1    Apr. 8, 2004

(51) Int. Cl.
*A61K 31/195*    (2006.01)
*A61K 31/19*    (2006.01)

(52) U.S. Cl. ............... 514/561; 514/557; 514/569; 514/970; 562/433; 564/194

(58) Field of Classification Search ........... 562/433; 514/557, 561, 569, 970; 564/194
See application file for complete search history.

(56) References Cited

U.S. PATENT DOCUMENTS

| | | | |
|---|---|---|---|
| 3,968,205 A | 7/1976 | Bickel | |
| 4,521,431 A | 6/1985 | Crookes | |
| 4,593,044 A * | 6/1986 | Metz | 514/557 |
| 4,711,906 A | 12/1987 | von Stetten et al. | |
| 4,879,303 A | 11/1989 | Davison et al. | |
| 5,096,926 A * | 3/1992 | Fiorini et al. | 514/569 |
| 5,128,373 A * | 7/1992 | Fiorini et al. | 514/569 |
| 5,414,011 A | 5/1995 | Fu et al. | |
| 5,534,242 A | 7/1996 | Henry | |
| 5,883,115 A | 3/1999 | Santus et al. | |
| 6,090,368 A | 7/2000 | Zia et al. | |
| 6,333,044 B1 | 12/2001 | Santus et al. | |
| 6,368,618 B1 | 4/2002 | Jun et al. | |
| RE37,727 E | 6/2002 | Hind | |
| 6,420,394 B1 | 7/2002 | Supersaxo | |

FOREIGN PATENT DOCUMENTS

WO    WO 99/15210    *    4/1999

OTHER PUBLICATIONS

Reinhart et al. "Postoperative analgesia . . . " CA 134:275616 (2000).*
RN 15307-8605.*
RN 15307-79-6.*
RN 137-58-6.*
RN 852473-08-6.*
Lee et al. "Pharmaceutically acceptable . . . ," CA 140:309382 (2004).*

* cited by examiner

*Primary Examiner*—Celia Chang
(74) *Attorney, Agent, or Firm*—Fei-Fei Chao; Andrews Kurth LLP

(57) ABSTRACT

The present invention provides pharmaceutically acceptable salts having local anesthetic and anti-inflammatory activities. The preferred pharmaceutically acceptable salt is a diclofenac salt of lidocaine. Diclofenac is a non-steroidal anti-inflammatory drug ("NSAID"). Lidocaine is a local anesthetic. Other NSAID (except the salicylic acid derivatives of NSAID) can be used to replace diclofenac and/or other local anesthetics can be used to replace lidocaine. The pharmaceutically acceptable salts are crystalline compounds, which are distinctively different from either the NSAID alone or the local anesthetic alone, as indicated by differential scanning calorimetry (DSC), thermogravimetric analysis (TGA), High Performance Liquid Chromatography (HPLC) and Fourier-Transformed Infrared Spectroscopy (FTIR) analyses. These pharmaceutically acceptable salts are suitable for use in topical treatment or parenteral injection to treat patients with localized pain, including muscle pain, joint pain, pain associated with herpes infection, and wound pain (such as surgical wound, burn wound etc.).

26 Claims, 13 Drawing Sheets

PHARMACEUTICALLY ACCEPTABLE SALTS CONTAINING LOCAL ANESTHETIC AND ANTI-INFLAMMATORY ACTIVITIES AND METHODS FOR PREPARING THE SAME

FIELD OF THE INVENTION

The present invention relates to a group of novel pharmaceutically acceptable salts, each containing local anesthetic and anti-inflammatory activities. The preferred pharmaceutical acceptable salt in this group is diclofenac salt of lidocaine. Diclofenac is a non-steroidal anti-inflammatory drug (NSAID). Lidocaine is a local anesthetic. Other NSAID (except the salicylic acid derivatives of NSAID) can be used to replace diclofenac and/or other local anesthetics can be used to replace lidocaine. The pharmaceutically acceptable salts of the present invention are physically and chemically different from either the NSAID alone or the local anesthetic alone. The pharmaceutically acceptable salts of the present invention are particularly suitable for use in topical treatment or parenteral injection to treat patients with localized pain, including, but not limited to, muscle pain, joint pain, pain associated with herpes infection, and/or wound pain (such as surgical pain or burn pain). The present invention also relates to methods for making the pharmaceutically acceptable salts.

BACKGROUND OF THE INVENTION

In the management of pain and discomfort, two kinds of drugs are widely used. The first kind is local anesthetics. Local anesthetics reversibly block the impulse conduction along nerves and other excitable membranes that primarily utilize sodium channels. Clinically, this action blocks the pain sensation from specific areas of the body.

Local anesthetics are weak bases. There are three major classes of local anesthetics, which are ester derivatives (such as cocaine, procaine etc.), amide derivatives (such as lidocaine, bupivacaine etc.), and others (such as dyclonine, pramoxine etc.). For therapeutic application, local anesthetics are usually made available as salts for reasons of solubility and stability. In the body, they exist either as the uncharged base (i.e., "free base") or as a cation.

Local anesthetics generally consist of a lipophilic group (frequently an aromatic ring) connected by an intermediate chain (commonly including an ester or amide) to an ionizable group (usually a tertiary amine). Optimal activity requires a delicate balance between the lipophilic and hydrophilic strengths of these groups. Since ester links (as in procaine) are more prone to hydrolysis than amide links, esters usually have a shorter duration of action. (Miller & Hondeghem, (1995), "Local Anesthetics" in *Basic & Clinical Pharmacology*, 6$^{th}$ Edition, Ed. by Katzung).

Local anesthetics are usually administered by injection into the area of the nerve fibers to be blocked. Thus, absorption and distribution are not as important in controlling the onset of effect as in determining the rate of offset of anesthesia and the likelihood of central nervous system and cardiac toxicity. Topical application of local anesthetics, however, requires drug diffusion for both onset and offset of anesthetic effect. Therefore, the solubility and stability of the drug becomes major factors in determining the therapeutic effects of the drug. (Miller & Hondeghem, (1995), "Local Anesthetics" in *Basic & Clinical Pharmacology*, 6$^{th}$ Edition, Ed. by Katzung).

Among the local anesthetics, lidocaine, 2-(diethylamino)-N-(2,6-dimethylphenyl)-acetamide, is particularly known for its treatment of ventricular tachycardia (an arrythmia of the heart) as an intravenous injection solution. (See e.g., U.S. Pat. No. 3,968,205). Lidocaine is also widely used as a vasoconstrictor to reduce regional blood flow in topical applications or aerosols (such as nasal aerosols to reduce nasal congestion). (See eg., U.S. Pat. No. 5,534,242). In addition, lidocaine is known for its therapeutic effects in reducing post-herpetic neuralgia (PHN) nerve injury pain from shingles (herpes zoster and post herpetic neuralgia) and analogous neuropathies. For example, U.S. Pat. No. RE37,727 discloses methods employing lidocaine intradermal administration by transport lidocaine from the skin surface, using patches and dressings, into the skin.

Lidocaine base is freely lipid soluble. It is insoluble in water and thus not suitable for use in an aqueous suspension, requiring ethanol or the like to obtain a liquid solution. However, its salt form, lidocaine-HCl, is very soluble in water and alcohol. Thus, lidocaine-HCl is generally the form that is used for preparation of injection solution.

Non-steroidal anti-inflammatory drugs (NSAIDs) are among the most widely used drugs, probably due to their therapeutic properties as anti-inflammatories, analgesics, anti-pyretics, and anti-thrombolics and are used to treat a variety of clinical conditions manifesting such symptoms as pain, inflammation, fever, and to treat and prevent atherosclerosis. While these drugs are highly effective, oral administration of many NSAIDs can cause serious adverse effects such as gastrointestinal bleeding and ulceration, liver and kidney damages, and central nervous system and cutaneous disturbances, particularly after extended use. Therefore, in an effort to minimize the adverse effects associated with oral administration, non-oral delivery of NSAIDs has been extensively investigated in recent years.

Transdermal delivery, in particular, is an attractive option because it avoids the hepatic first-pass metabolism, reduces the side effects associated with oral administration, is associated with higher patient compliance and, in some cases, enhances therapeutic efficacy of the drug.

Transdermal delivery of NSAIDs is particularly useful for treatment of rheumatoid arthritis and related conditions, which are characterized by painful and swollen joints due to inflammation in the musculoskeletal tissues of the joints. However, although topical administration of certain NSAIDs, such as naproxen, ketoprofen, diclofenac, piroxicam and ibuprofen, has been shown to deliver the drug to the local musculoskeletal tissues of joints where arthritic conditions often develop, due to the low solubility of NSAIDs in water, the effectiveness of topical administration of NSAIDs is limited by the inability of these drugs to permeate the skin.

In the conventional topical formulations of NSAIDs that are commercially available, the active ingredients are simply dissolved, dispersed or otherwise formulated in a suitable pharmaceutical vehicle. The thermodynamic activity of the drug in such formulations is relatively low due to the limited solubility of drugs in the vehicle. In recent years, improvement of the dermal permeation of NSAIDs has been introduced, which includes the increase of lipophilicity of the drug, the incorporation of the drug into lipid vesicles such as liposomes, and the employment of a permeation enhancer in the formulation. However, the results of these approaches are largely unsatisfactory.

Recently, U.S. Pat. No. 6,368,618 B1 discloses a topical formulation for delivery of NSAIDs using a two phase liquid composition containing aqueous and oil phases. U.S. Pat.

No. 6,420,394 discloses yet another topical pharmaceutical formulations for NSAIDs, which includes the addition of sodium phosphate buffer and optionally an alcoholic solvent to increase the permeation of NSAIDs. However, based on the facts that the absence of effective transdermal formulations of NSAIDs in the marketplace, efforts directed toward improving the delivery system of NSAIDs are desperately needed.

Contrary to local anesthetics, NSAIDs are weak acid. There are roughly nine major classes of NSAIDs, which are salicylate derivatives (such as acetosalicylate [aspirin]), propionic acid derivatives (such as ibuprofen), aniline derivatives (such as aminophenolacetaminophen [tylenol]), pyrazole derivatives (such as phenylbutazone), N-arylanthranilic acid (or fenamates) derivatives (such as meclofenamate), indole derivatives (such as indomethacin), acetic acid derivatives (such as diclofenac), oxicam derivatives (such as piroxicam), and miscellaneous others (such as celecoxib).

Among the NSAIDs, diclofenac, which is 2-(2,6-dichloro-anilino)-phenyl-acetic acid, is particularly known for its role as an anti-rheumatic agent for treatment of rheumatoid arthritis. Diclofenac belongs to the acetic acid class of NSAID. Due to its relatively low solubility in water, an aqueous injection solution of diclofenac is difficult to achieve.

U.S. Pat. No. 4,711,906 discloses a liquid diclofenac preparation where a better dissolution of the diclofenac is obtained when a local anesthetic, lidocaine, is added. This liquid diclofenac preparation is particularly suitable for use as injection solution.

Another NSAID similar to diclofenac and also belongs to the acetic acid class of NSAIDs is ketorolac. Ketorolac is comparable to opioids in terms of providing pain relief. For example, the overall analgesic effect of 30 mg of ketorolac is equivalent to that of 6 to 12 mg of Morphine.

Ketorolac is (±)-5-benzoyl-2,3-dihydro-1H-pyrrolizine-1-carboxylic acid. It is a derivative of pyrrolizine carboxylic acid and is structurally related to tolmetin and zomepirac. Like diclofenac, the free acid form of ketorolac has very low solubility in water. The most commonly used salt form of ketorolac is ketorolac tromethamine, which is much more water soluble than the free acid form of ketorolac.

There are various dosage forms/formulations for ketorolac tromethamine. For example, U.S. Pat. No. 6,090,368 discloses a pharmaceutical composition comprising ketorolac tromethamine admixed with an aqueous bioadhesive cellulosic polymer containing microcrystalline particles. The pharmaceutical composition is particularly useful for use in nasal spray. U.S. Pat. No. 5,414,011 discloses an ophthalmic formulations consisting of ketorolac alone or in combination with an antibiotic drug, and a preservative system having a quaternary ammonium preservative and a nonionic polyoxyethylated octylphenol surfactant. U.S. Pat. No. 5,883,115 discloses a transdermal delivery of an eutomer of ketorolac.

Ketorolac is a chiral drug which contains racemic mixture of [−]S form and [+]R form. The biological activity of ketorolac is with the S form. An eutomer is the stereoisomer of a chiral drug that exhibits greater pharmaceutical activity than its counterpart stereoisomer. In this case, the eutomer is the S form of ketorolac. U.S. Pat. No. 6,333,044 discloses a therapeutic composition of the racemic active form of ketorolac (i.e., the S form), in combination with a pharmaceutically acceptable excipient or diluent, for use in intranasal administration.

In the invention to be presented below, a group of novel pharmaceutically acceptable salts containing local anesthetic and anti-inflammatory effects is introduced. These pharmaceutically acceptable salts can be categorized as a "NSAID salt of a local anesthetic." These salts are further characterized by their unique physical and chemical properties, which resemble neither NSAIDs nor local anesthetics that they are originated from. These pharmaceutically acceptable salts not only have improved therapeutic activities for pain relief, but also demonstrate far much better solubility when used in parenteral injection and transdermal permeation when used in topical treatments.

SUMMARY OF THE INVENTION

The present invention provides novel pharmaceutically acceptable salts, each containing a local anesthetic and anti-inflammatory activity. The preferred one is a diclofenac salt of lidocaine, which has unique characteristics distinguishable from either diclofenac alone or lidocaine alone, based on the testing results in differential scanning colorimetry (DSC), thermo-gravimetric analysis (TGA), and Fourier-Transformed Infrared Spectroscopy (FTIR). Diclofenac belongs to the group of non-steroidal anti-inflammatory drug (NSAID). Lidocaine is a member of a group of local anesthetics.

The diclofenac portion of the salt is freely replaceable with another NSAID, as long as the NSAID is not a salicylic acid derivative; the lidocaine portion of the salt is also freely replaceable with another local anesthetic to form another pharmaceutically acceptable salt of the present invention.

Examples of the NSAID that can be used to replace diclofenac include, but are not limited to, etodolac, ketorolac, bromfenac, ibuprofen, fenoprofen, fluriboprofen, ketoprofen, naproxen, suprofen, meclofenamate, mefenamic acid, piroxicam, meloxicam, indomethacin, sulindac, phenylbutazone, oxyphenbutazone, tolmetin, and celecoxib. Among these NSAIDs, ketorolac is the preferred one.

Examples of the local anesthetics that can be used to replace lidocaine include, but are not limited to, butacaine, chloroprocaine, cocaine, cyclomethycaine, hexyclaine, procaine, proparacaine, propoxycaine, tetracaine, benzocaine, bupivacaine, dibucaine, etidocaine, lidocaine, mepivacaine, ropivacaine, prilocaine, dyclonine, and pramoxine.

The present invention also includes a method for making the pharmaceutically acceptable salts which include: (1) dissolving a lidocaine and a diclofenac in a solvent to form a drug mixture; and (2) removing the solvent from the drug mixture to form the pharmaceutically acceptable salt. The lidocaine and the diclofenac are either dissolved in the solvent respectively or mixed together prior to dissolving in the solvent. The lidocaine is either a free base of lidocaine or lidocaine-HCl. The diclofenac is a free acid of diclofenac, sodium diclofenac, potassium diclofenac, or diethylamine diclofenac.

The lidocaine portion of the salt is freely replaceable with a free base or a salt of another local anesthetic. The diclofenac portion of the salt is also freely replaceable a free acid or a salt of another NSAID as long as the NSAID is not a salicylic acid derivative.

Any solvent that is capable of dissolving NSAID and local anesthetic is suitable for use in the present invention. The preferred ones include, but are not limited to, methanol, ethanol, isopropyl alcohol, acetone, toluene, chloroform, dimethylformamide, dimethylacetamide, dimethylsulfoxide, methylene chloride and acetonitrile.

Any conventional methods that can be used to remove the solvent can be used for removing the solvent from the pharmaceutically acceptale salts of the present invention. The preferred methods for removing the solvent include, but are not limited to, crystallized by natural evaporation, vacuum condensation, or drying under nitrogen.

Another method for making the pharmaceutically acceptable salt of the present invention includes: (1) mixing a lidocaine and a diclofenac to form a drug mixture; and (2) pulverizing the drug mixture by a physical-mechanical means to form the pharmaceutically acceptable salt of the present invention. An example of the physical-mechanical meas is by pulverizing the drug mixture in a motar with a pestle. The lidocaine that can be used in this method includes, but is not limited to, a free base of lidocaine or lidocaine-HCl. The diclofenac that can be used in this method includes, but is not limited to, a free acid of diclofenac, sodium diclofenac, potassium diclofenac, or diethylamine diclofenac. Additionally, the diclofenac salt of lidocaine can be further purified by dissolving the salt in a suitable solvent followed by evaporating the solvent by natural evaporation, vacuum condensation, or drying under nitrogen.

Furthermore, the lidocaine portion of the salt is freely replaceable with a free base or salt of another local anesthetic. The diclofenac portion of the salt is also freely replaceable with a free acid or salt of another NSAID as long as the NSAID is not a salicylic acid derivative.

The present invention also provides a pharmaceutical formulation which comprises the diclofenac salt of lidocaine and a pharmaceutically acceptable carrier. The pharmaceutical formulation is suitable for use in topical treatment, such as in the forms of solution, gel, emugel, cream, ointment, lotion, transdermal patch, or eye drop. The pharmaceutical formulation is also suitable for parenteral injection.

The pharmaceutical formulation of the present invention is particularly suitable for use in treating patients with localized pain, such as muscle pain, joint pain, pain associated with herpes infection, and wound pain, by topically and parenterally treating these patients with an effective amount of the pharmaceutical formulation.

DETAILED DESCRIPTION OF THE INVENTION

Figure 1:
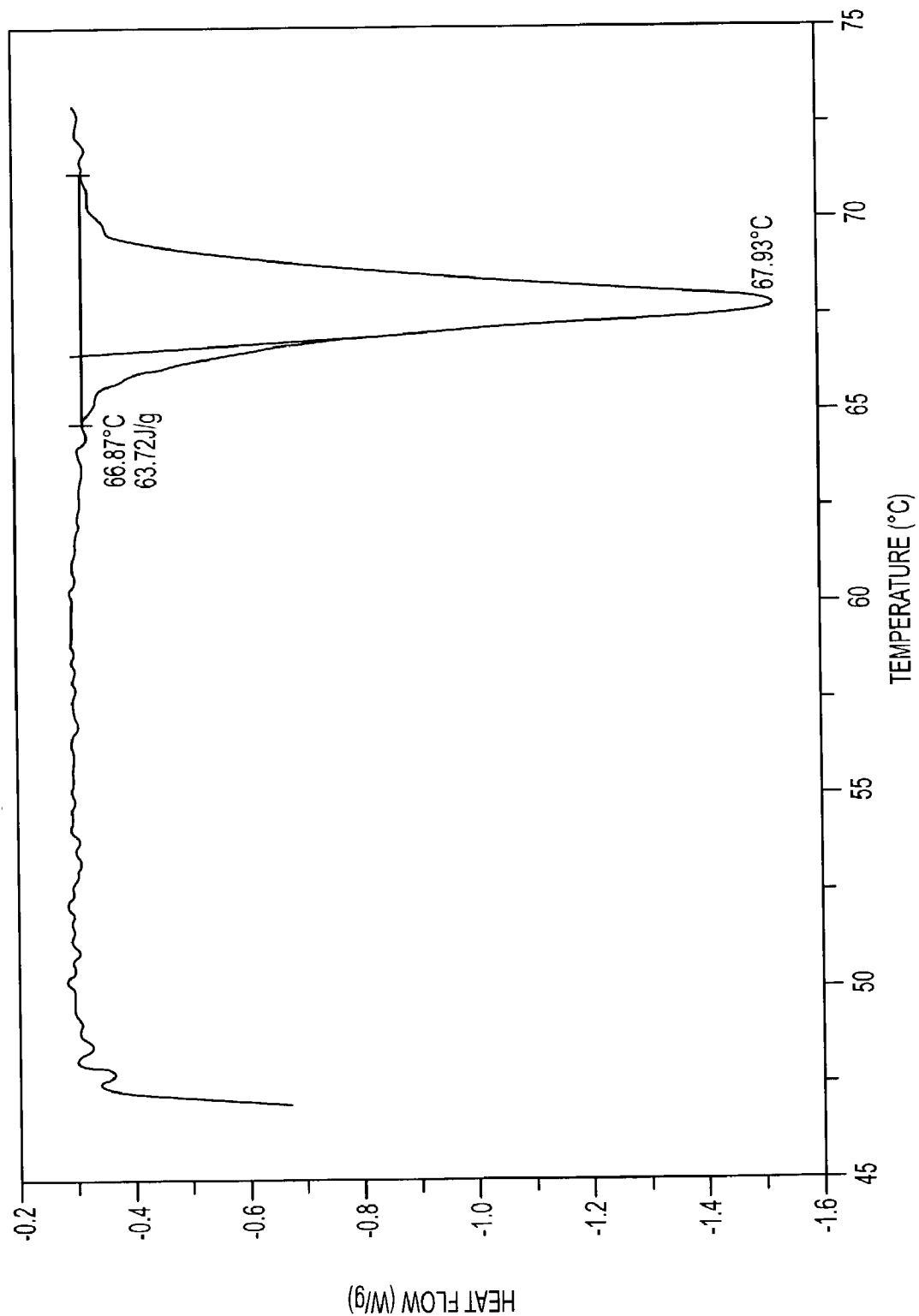
FIG. 1 shows a thermogram of differential scanning calorimetry (DSC) spectrum of free base of lidocaine. DSC was run at a heating rate of 2° C. per min using DSC V4. OB DuPont Model 2000. The onset temperature of the compound was at 66.87° C. The endothermal maximum of melting was at 67.93° C.

The present invention provides novel pharmaceutically acceptable salts which exhibit combined therapeutic effects of local anesthetic and anti-inflammatory activities. These pharmaceutical acceptable salts are an "NSAID salt of a local anesthetic agent." They are characterized by their distinctive physical and chemical properties, which are different from either the NSAID alone or the local anesthetic agent alone, as demonstrated by the DSC, TGA, HPLC, and FTIR analyses as shown in FIGS. 1–13.

The "NSAID salt of the local anesthetic agent" are formed by (1) the interaction of the weak acid (NSAID) with the weak base (local anesthetic); and (2) the solvent dissolution-removal or pulverization method employed in the present invention which further enhances the salt forming process. The "NSAID salt of the local anesthetic agent" is readily filtered and easily dried, and, if necessary, can be easily re-purified by re-dissolving the salt in a suitable solvent followed by drying to remove the solvent.

The pharmaceutically acceptable salts of the present invention are prepared in accordance with the following methods:

Method 1: A chosen NSAID, in its free acid form, is dissolved in a suitable solvent. A chosen local anesthetic agent, in its free base form, is dissolved in the same solvent. The dissolved NSAID and local anesthetic agent are mixed to form a mixed solution. The solvent is removed to produce the pharmaceutically acceptable salt of the present invention. Optionally, the pharmaceutically acceptable salt can be further purified by re-dissolving the salt in a solvent followed by drying to remove the solvent.

Method 2: A chosen NSAID and a chosen local anesthetic agent, each in its respective free acid or free base form, are uniformly mixed and dissolved in a suitable solvent. The solvent is then removed to produce the pharmaceutically acceptable salt of the present invention. Optionally, the pharmaceutically acceptable salt can be further purified by re-dissolving the salt in a solvent followed by drying to remove the solvent.

Method 3: A chosen NSAID and a chosen local anesthetic agent, each in its respective free acid or free base form, are uniformly mixed and pulverize using a physical-mechanical means to produce the pharmaceutically acceptable salt of the present invention. Optionally, the pharmaceutically acceptable salt can be re-purified by re-dissolving the salt in a suitable solvent followed by removing the solvent by vacuum evaporation or under nitrogen.

Method 4: A chosen NSAID and a chosen local anesthetic, each in its respective salt form, are either respectively dissolved in a suitable solvent and then mixed together as indicated in Method 1, or uniformly mixed and then dissolved in a suitable solvent as indicated in Method 2. Optionally, the dissolved mixture is heated to an elevated temperature (which is determined based on the solvent used in dissolving the compounds) followed by cooling to facilitate the formation of the salt. Optionally, the salt can be further purified by re-dissolving the salt in a solvent followed by drying to remove the solvent.

Method 5: A chosen NSAID and a chosen local anesthetic agent, each in its respective salt form, are mixed and then pulverized using physical-mechanical means to produce the pharmaceutically acceptable salt of the present invention. Optionally, the salt can be further purified by re-dissolving the salt in a solvent followed by drying to remove the solvent.

The pharmaceutically acceptable salts of the present invention have been confirmed by the following instrumental analyses to be distinctively different from the local anesthetic agent and/or the NSAID they originated:

Thermal Analysis: Two thermal analysis, thermogravimetric analysis (TGA) and differential scanning calorimetry (DSC) were employed. TGA measures the change in the mass of sample as the temperature is changed. The profile of the overall thermogravimetric weight loss versus temperature curve provides reliable indication of the phase and weight changes of the pharmaceutical compounds.

DSC examines the changes in physical properties of the pharmaceutical compound with temperature or time. During operation, DSC heats the test sample, measures heat flow between the test sample and its surrounding environment, and records a test thermogram of the test sample based on the measured heat flow. DSC provides information regarding the onset temperature, the endothermal maximum of melting, and the enthalpy of the pharmaceutical compound.

High Performance Liquid Chromatography (HPLC): Pharmaceutical compounds can be characterized and/or purified by HPLC. Alternatively, the content and/or purity of the pharmaceutical compounds can be determined by HPLC method. For a given column packing, solvent system, and flow rate, most compounds tend to elute to a certain degree from an analytical and/or preparative HPLC column.

UV Spectroscopy: The UV spectroscopy can be used to perform qualitative analysis of the pharmaceutical compounds.

Infrared (IR) Spectroscopy including Fourier-Transformed Infrared Spectroscopy (FTIR): Functional groups of a pharmaceutical compound can be determined by IR spectra based on their respective light transmittance. The IR spectrum of a pharmaceutical compound is presented in a drawing in which the ordinate is the transmittance in % and the abscissa is the wavelength in $cm^{-1}$. The IR is extremely sensitive to the structure, conformation, and environment of an organic compound and thus is a suitable method for the characterization and identification of different solid forms of drugs. An FTIR microscope allows the measurement of the IR spectrum of a single crystal or group of crystals. The microscope technique minimizes the possibility of obtaining IR spectra of mixture of crystal forms and is a distinct advantage over approaches that use powdered samples.

Liquid Chromatography-Mass Spectroscopy (LC-MS): The molecular weight and the chemical structure of the pharmaceutical compound can be determined using the liquid chromatography-mass spectroscopy (LC-MS) method.

Transdermal Absorption Test: The transdermal absorption of the pharmaceutical compound can be determined using the transdermal diffusion measurement instrument.

Local anesthetic agents are basic compounds. They are capable of forming pharmaceutically acceptable acid addition salts of the compounds with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts. In the examples and experimental results to be presented in the following section (infra), an NSAID is proven to be an acid addition salt of the local anesthetic agents.

NSAIDs are acidic compounds. They can form pharmaceutically acceptable base addition salts of the compounds with organic and inorganic bases by conventional methods.

Examples of the nontoxic alkali metal and alkaline earth bases include, but are not limited to, calcium, sodium, potassium and ammonium hydroxide; and nontoxic organic bases include, but are not limited to, triethylamine, butylamine, piperazine, and tri(hydroxymethyl)-methylamine. In the examples and experimental results to be presented in the following sections, a local anesthetic is proven to be a base addition salt of the NSAIDs.

Local anesthetics that are utilized to prepare the pharmaceutical compounds of the present invention include, but are not limited to the following classes of compounds: esters (e.g., butacaine, chloroprocaine, cocaine, cyclomethycaine, hexylcaine, procaine, proparacaine, propoxycaine, tetracaine, benzocaine), amide (e.g., bupivacaine, dibucaine, etidocaine, lidocaine, mepivacaine, ropivacaine, prilocaine), dyclonine, pramoxine and the pharmaceutically acceptable salts of the above compounds.

The NSAIDs that are suitable for preparation of the pharmaceutical compounds of the present invention include, but are not limited to: acetic acid derivatives (eg, diclofenac, etodolac, ketorolac, and bromfenac), propionic acid derivatives (eg, ibuprofen, fenoprofen, fluriboprofen, ketoprofen, naproxen, suprofen), fenamates (eg, meclofenamate, mefenamic acid), oxicam (eg, piroxicam, meloxicam), indole derivatives (eg., indomethacin, sulindac), pyrazolone derivatives (eg, phenylbutazone, oxyphenbutazone), tolmetin, celecoxib, and the pharmaceutically acceptable salts of the above compounds. The preferred NSAIDs are diclofenac and ketorolac.

In addition, when comparing to the individual NSAIDs and local anesthetics, the pharmaceutically acceptable salts of the present invention, which are prepared by mixing equal moles of NSAIDs and local anesthetics together followed by crystallization, possess improved aqueous solubility as well as enhanced transdermal absorption of the skin. These improvements enable the preparations of the pharmaceutically acceptable salts in many different formulations with ease which in turn offer more treatment options to the patients. These improvements simplify the manufacturing process and maintain the product quality of the pharmaceutically acceptable salts of the present invention.

The pharmaceutical acceptable salts of the present invention are particularly suitable for formulations as injection solution and/or topical preparations. In the injection solution, the pharmaceutically acceptable salts are preferably first dissolved in benzyl alcohol. The dissolved pharmaceutical acceptable salts are then mixed with methyl paraben and propyl paraben, before the addition of water.

Formulations suitable for topical administration include liquid or semi-liquid preparations suitable for penetration through the skin to the site of where treatment is required. Examples of liquid preparations include, but are not limited to topical solution or drops (such as eye, ear, or nose drops). Examples of semi-liquid preparations include, but are not limited to liniments, lotions, creams, ointment or paste, gel, emugel. The pharmaceutical ingredients are in general those commonly used and generally recognized by person skilled in the art of pharmaceutical formulation.

Topical solution or eye drops of the present invention may contain aqueous or oily solution or suspensions. They may be prepared by dissolving the pharmaceutical compound in a suitable aqueous solution of a bactericidal and/or fungicidal agent and/or any other suitable preservative, and preferably including a surface active agent. For eye drops, it is preferred that the resulting solution be clarified by filtration, transferred to a suitable container which is then sealed and sterilized by autoclaving. As for other topical preparations, sterilization is generally not required.

Examples of bactericidal and fungicidal agents suitable for inclusion in the drops include, but are not limited to, phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol. Optionally, L-menthol can be added to the topical solution.

Lotions and liniments according to the present invention include those suitable for application to the skin, which contain a sterile aqueous solution and optionally a bactericide. They may also include an agent to hasten drying and cooling of the skin, such as alcohol or acetone, and/or a moisturizer such as glycerol or an oil such as castor oil or arachis oil.

Cream, ointments or pastes are semi-solid formulations. They may be made by mixing the pharmaceutically acceptable salts in finely-divided or powdered form, alone or in solution or suspension in an aqueous or non-aqueous fluid, with the aid of suitable machinery, with a greasy or non-greasy base. The base may contain hydrocarbons. Examples of the hydrocarbons include, but are not limited to, hard, soft, or liquid paraffin, glycerol, beeswax, a metallic soap, a mucilage, an oil of natural origin (such as almond, corn, arachis, castor or olive oil), wool fat or its derivative, and/or a fatty acid (such as stearic acid or oleic acid). The formulation may also contain a surface active agent, such as anionic, cationic or non-ionic surfactant. Examples of the surfactants include, but are not limited to, sorbitan esters or polyoxyethylene derivatives thereof (such as polyoxyethylene fatty acid esters), and carboxypolymethylene derivatives thereof (such as carbopol). Suspending agents such as natural gums, cellulose derivatives inorganic materials such as silicaceous silicas, and other ingredients such as lanolin, may also be included. For ointment, polyethylene glycol 540, polyethylene glycol 3350, and propyl glycol may also be used to mixed with the pharmaceutical compound.

A gel or emugel formulation of the present invention includes any gel forming agent commonly used in pharmaceutical gel formulations. Examples of gel forming agents are cellulose derivtives such as methyl cellulose, hydroxyethyl cellulose, and carboxymethyl cellulose; vinyl polymers such as polyvinyl alcohols, polyvinyl pyrrolidones; and carboxypoly-methylene derivatives such as carbopol. Further gelling agents that can be used for the present invention are pectins, gums (such as gum arabic and tragacanth, alginates, carrageenates, agar and gelatin). The preferred gelling agent is carbopol. Furthermore, the gel or emugel formulation may contain auxiliary agents commonly used in this kind of formulations such as preservatives, antioxidants, stabilizers, colorants and perfumes.

The following examples are illustrative, but not limiting the scope of the present invention. Reasonable variations, such as those occur to reasonable artisan, can be made herein without departing from the scope of the present invention.

EXAMPLE 1

Preparation of a Diclofenac Salt of Lidocaine by Lidocaine Free Base and Diclofenac Free Acid The diclofenac salt of lidocaine in Example 1 contained the following ingredients:

| Ingredients | Weight (g) or Volume (ml) |
|---|---|
| Lidocaine Free Base | 23.434 g |
| Diclofenac Free Acid | 29.615 g |
| Alcohol | 120 mL |

Method 1:

Lidocaine free base (23.434 g) was dissolved in 20 mL of alcohol. Diclofenac Free acid (29.615 g) was dissolved in 100 mL of alcohol. The dissolved lidocaine free base and diclofenac free acid solutions were thoroughly mixed. The diclofenac salt of lidocaine of Example 1 was obtained by removing the alchohol by natural evaporation (i.e., by allowing the sample to be naturally evaporated), reduced-pressure or vacuum condensation, or drying under nitrogen until complete dryness.

Method 2:

Lidocaine free base (23.434 g) and diclofenac free acid (29.615 g) were thoroughly mixed and then added to 120 mL of alcohol. Alternatively, lidocaine free base and diclofenac free acid were sequentially added to alcohol. The resultant mixture was then stirred until the mixture were dissolved. The diclofenac salt of lidocaine of Example 1 was obtained as removing the alcohol by natural evaporation, reduced-pressure or vacuum condensation, or drying under nitrogen until the sample was completely dried.

EXAMPLE 2

Preparation of A Diclofenac Salt of Lidocaine BV Lidocaine Free Base and Diclofenac Free Acid The diclofenac salt of lidocaine of Example 2 contained the following ingredients:

| Ingredients | Weight (g) or Volume (ml) |
|---|---|
| Lidocaine Free Base | 2.3434 g |
| Diclofenac Free Acid | 2.9615 g |
| Alcohol | 120 mL |

Method 1:

Lidocaine free base (2.3434 g) was dissolved in 20 mL of alcohol. Diclofenac free acid (2.9615 g) was dissolved in 100 mL alcohol with optional heating to facilitate dissolution. The dissolved solutions of lidocaine free base and diclofenac free acid were mixed. The diclofenac salt of lidocaine of Example 2 was obtained by removing the alcohol by natural evaporation, reduced-pressure or vacuum condensation, or drying under nitrogen until the sample was completely dried.

Method 2:

Lidocaine free base (2.3434 g) and diclofenac free acid (2.9615 g) were thoroughly mixed and then added to 120 mL alcohol. Alternatively, lidocaine free base and diclofenac free acid were sequentially added to alcohol. The resultant mixture was then stirred until the mixture was dissolved. The diclofenac salt of lidocaine of Example 2 was obtained by removing the alcohol by natural evaporation, reduced-pressure or vacuum condensation, or drying under nitrogen until the sample was completely dried.

EXAMPLE 3

Preparation of a Diclofenac Salt of Lidocaine by Lidocaine Free Base and Diclofenac Free Acid The diclofenac salt of lidocaine of Example 3 contained the following ingredients:

| Ingredients | Weight (g) or Volume (ml) |
|---|---|
| Lidocaine Free Base | 23.434 g |
| Diclofenac Free Acid | 29.615 g |
| Isopropyl Alcohol | 120 mL |

Method 1:

Lidocaine base (23.434 g) was dissolved in 20 mL of isopropyl alcohol. Diclofenac acid (29.615 g) was dissolved in 100 mL of isopropyl alcohol with optional heating to facilitate the dissolution. The dissolved solutions of lidocaine and diclofenac were mixed. The diclofenac salt of lidocaine of Example 3 was obtained by removing the isopropyl alcohol by nature evaporation, reduced-pressure or vacuum condensation, or drying under nitrogen until the sample was completely dried.

Method 2:

Lidocaine free base (23.434 g) and diclofenac free acid (29.615 g) were mixed and then added to 120 mL of isopropyl alcohol. Alternatively, lidocaine free base and diclofenac free acid were seqentially added to isopropyl alcohol. The resultant mixture was then stirred until the mixture was completely dissolved. The diclofenac salt of lidocaine of Example 3 was obtained by removing the isopropyl by natural evaporation, reduced-pressure or vacuum condensation, or drying under nitrogen until the sample was completely dried.

EXAMPLE 4

Preparation of a Diclofenac Salt of Lidocaine by Lidocaine Free Base and Diclofenac Free Acid The diclofenac salt of lidocaine of Example 4 contained the following ingredients:

| Ingredients | Weight (g) or Volume (ml) |
|---|---|
| Lidocaine Free Base | 23.434 g |
| Diclofenac Free Acid | 29.615 g |
| Acetone | 210 mL |

Method 1:

Lidocaine free base (23.434 g) was dissolved in 10 mL acetone. Diclofenac free acid (29.615 g) was dissolved in 210 mL of acetone with optional heating to facilitate the dissolution. The dissolved solutions of lidocaine free base and diclofenac free acid were thoroughly mixed. The diclofenac salt of lidocaine of Example 4 was obtained by removing the acetone by natural evaporation, reduced-pressure or vacuum condensation, or drying under nitrogen until the sample was completely dried.

Method 2:

Lidocaine free base (23.434 g) and diclofenac free acid (29.615 g) were mixed and then added to 210 mL of acetone. Alternatively, lidocaine free base and diclofenac free acid were sequentially added to acetone. The resultant mixture was then stirred until the mixture was completely dissolved. The diclofenac salt of lidocaine of Example 4 was obtained by removing the acetone by natural evaporation, reduced-pressure or vacuum condensation, or drying under nitrogen, until the sample was completely dried.

EXAMPLE 5

Preparation of a Diclofenac Salt of Lidocaine by Lidocaine Free Base and Diclofenac Free Acid The diclofenac salt of lidocaine of Example 5 contained the following ingredients:

| Ingredients | Weight (g) or Volume (ml) |
|---|---|
| Lidocaine Free Base | 23.434 g |
| Diclofenac Free Acid | 29.615 g |
| Toluene | 500 mL |

Method 1

Lidocaine free base (23.434 g) was dissolved in 500 mL toluene. Diclofenac free acid (29.615 g) was added to the toluene solution containing dissolved lidocaine free base. The mixture was stirred until complete dissolution. The diclofenac salt of lidocaine of Example 5 was obtained by removing the toluene by natural evaporation, reduced-pressure or vacuum condensation, or drying under nitrogen, until the sample was completely dried.

Method 2:

Lidocaine free base (23.434 g) and diclofenac free acid (29.615 g) were mixed and then added to 500 mL of toluene. Alternatively, lidocaine free base and diclofenac free acid were mixed or sequentially added to toluene. The resultant mixture was then stirred until the mixture was dissolved. The diclofenac salt of lidocaine of Example 5 was obtained by removing the toluene by natural evaporation, reduced-pressure or vacuum condensation, or drying under nitrogen, until the sample was completely dried.

EXAMPLE 6

Preparation of a Diclofenac Salt of Lidocaine by Lidocaine-HCl and Diclofenac-Diethylamine The diclofenac salt of lidocaine of Example 6 contained the following ingredients:

| Ingredients | Weight (g) or Volume (ml) |
|---|---|
| Lidocaine-HCl | 25 g |
| Diclofenac Diethylamine | 5.8 g |
| Isopropyl Alcohol | 100 mL |

Method 1:

Lidocaine-HCl (25 g) was dissolved in isopropyl alcohol. Diclofenac acid diethylamine (5.8 g) was dissolved in isopropyl alcohol. The diclofenac solution was added to the lidocaine solution and mixed to form a uniform solution. The diclofenac salt of lidocaine of Example 6 was obtained by removing the isopropyl alcohol by natural evaporation, reduced-pressure or vacuum condensation, or drying under nitrogen, until the sample was completely dried.

Method 2:

Lidocaine-HCl hydrochloride (25 g) and diclofenac diethylamine (5.8 g) were mixed and then added to 100 mL of isopropyl alcohol. The resultant mixture was then stirred until the mixture was completely dissolved. The diclofenac salt of lidocaine of Example 6 was obtained by removing the isopropyl alcohol by natural evaporation, reduced-pressure or vacuum condensation, or drying under nitrogen, until the sample was completely dried.

EXAMPLE 7

Preparation of a Topical Solution Containing a Diclofenac Salt of Lidocaine Made by Lidocaine Free Base and Diclofenac Free Acid The topical solution of Example 7 contained the following ingredients:

| Ingredients | Weight (g) or Volume (ml) |
|---|---|
| Diclofenac Free Acid | 29.615 g |
| Lidocaine Free Base | 23.434 g |
| L-Menthol | 2 g |
| Acetone | 210 mL |
| Alcohol | 5280 mL |
| Purified water | 2640 mL |
| TOTAL WEIGHT | 8000 mL |

Method:

(1) Lidocaine free base (23.434 g) was dissolved in acetone (10 mL) with stirring.

(2) Diclofenac free acid (29.615 ml) was dissolved in acetone 200 mL with stirring.

(3) The solutions of (1) and (2) were mixed to form a uniform solution. The resultant solution was condensed under reduced pressure to produce a pharmaceutical compound of the present invention.

(4) The pharmaceutical compound of (3) was dissolved in alcohol 4000 g.

(5) L-menthol (2 g) was added to the solution of (4) and mixed until complete dissolution. Purified water (2640 mL) was added to the resultant solution to a final volume of 8000 mL to produce the topical solution of the present invention.

EXAMPLE 8

Preparation of An Injection Solution Containing a Diclofenac Salt of Lidocaine Made By Lidocaine Free Base and Diclofenac Free Acid The injection solution of Example 8 contained the following ingredients:

| Ingredients | Weight (g) or Volume (ml) |
|---|---|
| Diclofenac Free Acid | 29.615 g |
| Lidocaine Free Base | 23.434 g |
| Acetone | 210 mL |

-continued

| Ingredients | Weight (g) or Volume (ml) |
|---|---|
| Benzyl Alcohol | 500 mL |
| Methyl Paraben | 1.8 mg |
| Propyl Paraben | 0.2 mg |
| Water For Injection | q.s. to 10000 mL |

Method:

(1) Lidocaine free base (29.615 g) was dissolved in acetone (10 mL) with stirring.

(2) Diclofenac free acid was dissolved in acetone (200 mL) with stirring.

(3) The solutions of (1) and (2) were mixed to form a uniform solution. The resultant solution was condensed under reduced pressure or vacuum condition to obtain a pharmaceutical compound of the present invention.

(4) The pharmaceutical compound of (3) was dissolved in benzyl alcohol (500 mL) with stirring. Optionally, mild heating was applied to facilitate the dissolution.

(5) Methyl paraben (1.8 mg) and propyl paraben (0.2 mg) were added to the solution of (4) and mixed until complete dissolution. The resultant solution was q.s. with water to a final volume of 10000 mL. The solution was then passed through a 0.22 μm filter to form the injection solution of the present invention.

EXAMPLE 9

Preparation of a Cream Containing a Diclofenac Salt of Lidocaine Made by Lidocaine Free Base and Diclofenac Free Acid The cream of Example 9 contained the following ingredients:

| Ingredients | Weight (g) or Volume (ml) |
|---|---|
| Diclofenac Free Acid | 29.615 g |
| Lidocaine Free Base | 23.434 g |
| Acetone | 210 mL |
| Polyoxyethylene fatty acid esters | 200 g |
| Carboxypolymethylene (Carbopol) | 50 g |
| Purified Water | 100 g |
| TOTAL WEIGHT | 1000 g |

Method:

(1) Lidocaine free base (29.615 g) was dissolved in acetone (10 mL) with stirring.

(2) Diclofenac free acid was dissolved in acetone (200 mL) with stirring.

(3) The solutions of (1) and (2) were mixed to form a uniform solution. The resultant solution was condensed under reduced pressure or vacuum condition to obtain a diclofenac salt of lidocaine of the present invention.

(4) The compound of (3) and polyoxyethylene fatty acid esters (200 g) were mixed and stirred with heating to form a uniform liquid.

(5) Carboxypolymethylene (50 g) and purified water (500 g) were mixed to form a uniform liquid.

(6) The liquids of (4) and (5) were mixed to form a uniform mixture. Purified water 196.951 g was added to the resultant mixture and stirred until a uniform mixture was formed to form the cream of the present invention.

EXAMPLE 10

Preparation of an Ointment Containing a Diclofenac Salt of Lidocaine Made by Lidocaine Free Base and Diclofenac Free Acid The ointment of Example 10 contained the following ingredients:

| Ingredients | Weight (g) or Volume (ml) |
|---|---|
| Diclofenac Free Acid | 29.615 g |
| Lidocaine Free Base | 23.434 g |
| Acetone | 210 mL |
| Polyethylene glycol 540 | 200 g |
| Polyethylene Glycol 3350 | 646.951 g |
| Propyl glycol | 100 g |
| TOTAL WEIGHT | 1000 g |

Method:

(1) Lidocaine free base (29.615 g) was dissolved in acetone (10 mL) with stirring.

(2) Diclofenac free acid was dissolved in acetone (200 mL) with stirring.

(3) The solutions of (1) and (2) were mixed to form a uniform solution. The resultant solution was condensed under reduced pressure or vacuum condition to obtain a diclofenac salt of lidocaine of the present invention.

(4) The compound of (3), polyethylene glycol 540 (200 g), and polyethylene glycol 3350 (646.951 g) were mixed and stirred with heat to form a uniform liquid.

(5) The mixture of (4) and propyl glycol were mixed and stirred until a uniform mixture was formed to produce the pharmaceutical ointment of the present invention.

EXAMPLE 11

Preparation of a Diclofenac Salt of Lidocaine Containing Lidocaine-HCl and Diclofenac-Sodium The pharmaceutical compound in Example 11 contained the following ingredients:

| Ingredients | Weight (g) or Volume (ml) |
|---|---|
| Lidocaine HCl | 28.884 g |
| Diclofenac Sodium | 31.813 g |
| Alcohol | 320 mL |

Method: 1

Lidocaine-HCl (28.884 g) was dissolved in 200 mL of alcohol. Diclofenac sodium (31.813 g) was dissolved in 120 mL of alcohol. The dissolved lidocaine-HCl and diclofenac sodium solutions were thoroughly mixed. The diclofenac salt of lidocaine of Example 11 was obtained by removing the alcohol by natural evaporation, vacuum condensation, or drying under nitrogen, until the sample was completely dried.

Method: 2

Lidocaine-HCl (28.884 g) and diclofenac sodium (31.813 g) were thoroughly mixed and then added to 320 mL of alcohol. Alternatively, lidocaine-HCl and diclofenac sodium were sequentially added to alcohol. The resultant mixture was then stirred until the mixture were dissolved. The diclofenac salt of lidocaine of Example 11 was obtained by removing the alcohol by natural evaporation, reduced-pressure or vacuum condensation, or drying under nitrogen, until the sample was completely dried.

EXAMPLE 12

Preparation of a Diclofenac Salt of Lidocaine by Lidocaine-HCl and Diclofenac-Sodium The diclofenac salt of lidocaine of Example 12 contained the following ingredients:

| Ingredients | Weight (g) or Volume (ml) |
| --- | --- |
| Lidocaine-HCl | 28.884 g |
| Diclofenac Sodium | 31.813 g |
| Isopropyl Alcohol | 320 mL |

Method: 1

Lidocaine-HCl (28.884 g) was dissolved in 120 mL of isopropyl alcohol. Diclofenac sodium (31.813 g) was dissolved in 200 mL of isopropyl alcohol. The solutions of lidocaine-HCl and diclofenac sodium were mixed. The diclofenac salt of lidocaine of Example 12 was obtained by removing the isopropyl alcohol by natural evaporation, reduced-pressure or vacuum condensation, or drying under nitrogen, until the sample was completely dried.

Method: 2

Lidocaine-HCl (28.884 g) and diclofenac sodium (31.813 g) were mixed and then added to 320 mL of isopropyl alcohol. Alternatively, diclofenac sodium and lidocaine hydrochloride were sequentially added to isopropyl alcohol. The resultant mixture was then stirred until the mixture was completely dissolved. The diclofenac salt of lidocaine of Example 12 was obtained by removing the isopropyl alcohol by natural evaporation, reduced-pressure or vacuum condensation, or drying under nitrogen until the sample was completely dried.

EXAMPLE 13

Preparation of a Ketorolac Salt of Lidocaine by Lidocaine Free Base and Ketorolac Free Acid The ketorolac salt of lidocaine pharmaceutical compound of Example 13 contained the following ingredients:

| Ingredients | Weight (g) |
| --- | --- |
| Ketorolac Free Acid | 25.5 g |
| Lidocaine Free Base | 23.434 g |
| Isopropyl Alcohol | 500 g |

Method: 1

Ketorolac free acid (25.5 g) was dissolved in isopropyl alcohol (300 mL) with stirring. Lidocaine free base (23.434 g) was dissolved with stirring in 200 mL isopropyl alcohol. The solutions of ketorolac and lidocaine were mixed to form a uniform solution. The ketorolac salt of lidocaine of the present invention was obtained by removing the isopropyl alcohol by natural evaporation, reduced-pressure or vacuum condensation, or drying under nitrogen until the sample was completely dried.

Method: 2

Ketorolac free acid and lidocaine free base were mixed and then added to isopropyl alcohol. Alternatively, ketorolac free acid and lidocaine free base were sequentially added to isopropyl alcohol. The resultant mixture was then stirred until the solids were dissolved. The ketorolac salt of lidocaine of the present invention was obtained by removing the isopropyl alcohol by natural evaporation, reduced-pressure or vacuum condensation, or drying under nitrogen, until the sample was completely dried.

EXAMPLE 14

Preparation of a Ketorolac Salt of Lidocaine by Lidocaine Free Base and Ketorolac Free Acid The ketorolac salt of lidocaine of Example 14 contained the following ingredients:

| Ingredients | Weight (g) |
| --- | --- |
| Ketorolac Free Acid | 25.5 g |
| Lidocaine Free Base | 23.434 g |
| Alcohol | 500 g |

Method: 1

Ketorolac free acid (25.5 g) was dissolved in alcohol (300 mL) with stirring. Lidocaine free base (23.434 g) was dissolved with stirring in 200 mL of alcohol. The solutions of ketorolac and lidocaine were mixed to form a uniform solution. The ketorolac salt of lidocaine of the present invention was obtained by removing the alcohol by natural evaporation, reduced-pressure or vacuum condensation, or drying under nitrogen until the sample was completely dried.

Method: 2

Ketorolac free acid and lidocaine free base were mixed and then added to alcohol. Alternatively, ketorolac free acid and lidocaine free base were sequentially added to alcohol. The resultant mixture was then stirred until the solids were dissolved. The ketorolac salt of lidocaine of the present invention was obtained by removing the alcohol by natural evaporation, reduced-pressure or vacuum condensation, or drying under nitrogen, until the sample was completely dried.

EXAMPLE 15

Preparation of An Injection Solution Containing A Ketorolac Salt of Lidocaine Made By Lidocaine Free Base and Ketorolac Free Acid The pharmaceutical compound of Example 15 contained the following ingredients

| Ingredients | Weight (g) or Volume (ml) |
| --- | --- |
| Ketorolac Free Acid | 25.5 g |
| Lidocaine Free Base | 23.434 g |

-continued

| Ingredients | Weight (g) or Volume (ml) |
|---|---|
| Alcohol | 500 g |
| Water For Injection | q.s. to 1000 mL |
| sodium chloride | 9 mg |

Method:

(1) Ketorolac free acid (25.5 g) was dissolved in alcohol (300 mL) with stirring.

(2) Lidocaine free base (23.434 g) was dissolved in alcohol (200 mL) with stirring.

(3) The solutions of ketorolac free acid and lidocaine free base were mixed to form a uniform solution. The solution was sterile-filtered and then condense under reduced pressure or vacuum condition to produce a pharmaceutical compound of the present invention.

(4) The compound of (3) was dissolved, with stirring, in 400 mL of purified water. Sodium chloride was added to the resultant solution and stirred until the sample was completely dissolved.

(5) Additional water was added to the solution of (4) to q.s. the a final volume to 1000 mL. The resultant aqueous solution was passed through a 0.22 µm filter to provide the sterile pharmaceutical injection solution of Example 15.

EXAMPLE 16

Preparation of a Ketorolac Salt of Lidocaine by Lidocaine Free Base and Ketorolac Free Acid The pharmaceutical compound of Example 16 contained the following ingredients:

| Ingredients | Weight (g) |
|---|---|
| Ketorolac Free Acid | 25.5 g |
| Lidocaine Free Base | 23.434 g |

Method:

Ketorolac free acid and lidocaine free base were mixed and then pulverized in a mortar with a pestle or using other physical mechanical forces to produce the ketorolac salt of lidocaine. The ketorolac salt of lidocaine could be further purified by dissolving the salt in a solvent followed by removing the solvent by evaporation, reduced-pressure or vacuum condensation, or drying under nitrogen.

EXAMPLE 17

Preparation of a Ketorolac Salt of Lidocaine by Lidocaine Hydrochloride and Ketorolac Tromethamine The diclofenac salt of lidocaine of Example 17 contained the following ingredients:

| Ingredients | Weight (g) |
|---|---|
| Ketorolac Tromethamine | 25 g |
| Lidocaine Hydrochloride | 28.884 g |

Method:

Ketorolac tromethamine (25 g) and lidocaine hydrochloride (28.884 g) were mixed and then pulverized in a mortar with a pestle or using other physical mechanical forces to produce the ketorolac salt of lidocaine. The ketorolac salt of lidocaine could be further purified by dissolving the sample in a solvent followed by removing the solvent by evaporation, reduced-pressure or vacuum condensation, or drying under nitrogen.

EXAMPLE 18

Preparation of a Diclofenac Salt of Lidocaine by Lidocaine Hydrochloride and Diclofenac Sodium The pharmaceutical compound of Example 18 contained the following ingredients:

| Ingredients | Weight (g) |
|---|---|
| Lidocaine Hydrochloride | 28.884 g |
| Diclofenac Sodium | 31.813 g |

Method:

Lidocaine hydrochloride (28.884 g) and diclofenac sodium (31.813 g) were mixed and then pulverized in a mortar with a pestle or using other physical mechanical forces to produce the diclofenac salt of lidocaine. The diclofenac salt of lidocaine could be further purified by dissolving the compound in a solvent followed by removing the solvent by evaporation, reduced-pressure or vacuum condensation, or drying under nitrogen.

EXAMPLE 19

Preparation of a Diclofenac Salt of Lidocaine by Lidocaine Free Base and Diclofenac Free Acid The diclofenac salt of lidocaine of Example 19 contained the following ingredients:

| Ingredients | Weight (g) |
|---|---|
| Lidocaine Free Base | 23.434 g |
| Diclofenac Free Acid | 29.615 g |

Method:

Lidocaine free base (23.434 g) and diclofenac (29.615 g) were mixed and then pulverized in a mortar with a pestle or using other physical mechanical forces to produce the diclofenac salt of lidocaine. The diclofenac salt of lidocaine could be further purified by dissolving the sample in a solvent followed by removing the solvent by evaporation, reduced-pressure or vacuum condensation, or drying under nitrogen.

The characteristics of the above Examples were further determined using the following instruments: (1) HPLC, (2) UV Spectroscopy, (3) FTIR, (4) LC-MS, (5) DSC, and (6) TGA. The results demonstrate that the pharmaceutically acceptable salts were compounds that were physically and chemically different from the NSAID alone or the local anesthetic agent alone, as shown by DSC thermogram, TGA weight loss profile, IR spectrum and HPLC.

The following Experimental Examples 1–4 are selective results of the pharmaceutically acceptable salts analyzed by HPLC (Experimental Example 1), DSC (Experimental Example 2), and TGA (Experimental Example 3) and FTIR (Experimental Example 4). These Experimental Examples are for illustrative purpose. They are not intended to limit the scope of the present invention. Reasonable variations, such as those occur to reasonable artisan, can be made herein without departing from the scope of the present invention.

EXPERIMENTAL EXAMPLE 1

HPLC Analysis of a Diclofenac Salt of Lidocaine Made by Lidocaine Free Base and diclofenac Free Acid HPLC analysis was conducted using a mobile phase containing n-hexane, 1,4-dioxane, ethanol, isopropyl alcohol, and water at a volume ratio of 560:320:120:4:2. The flow rate was at 1.2 ml/min. The compound was detected at a wavelength of 280 nm.

The pharmaceutically acceptable salt of Experimental Example 1 was prepared according to Example 1 (supra) by mixing equal moles of lidocaine free base and diclofenac free acid in alcohol followed by removing the alcohol by evaporation. If the resulting diclofenac salt of lidocaine was a simple mixture of lidocaine and diclofenac, the weight percents of the NSAID and the local anesthetic in the mixture should be unchanged, i.e., the resulting compound should have the same weight percentages as those of the individual NSAID and local anesthetic.

HPLC analysis of the weight percents of lidocaine free base (23.434 g) and diclofenac free acid (29.615 g) were 44% and 56% respectively in the mixture. However, the HPLC analysis of the diclofenac salt of lidocaine demonstrated weight percents of the lidocaine portion and the diclofenac portion as 43.2% and 57.4% respectively, indicating that the diclofenac salt of lidocaine differed from a mixture of lidocaine and diclofenac. In other words, a new compound, which was physically and chemically different from its parent compounds, lidocaine and diclofenac, was formed.

EXPERIMENTAL EXAMPLE 2

Differential Scanning Calorimetry (DSC) Analysis of a Diclofenac Salt of Lidocaine Made by Lidocaine Free Base-Diclofenac Free Acid Lidocaine free base, diclofenac free acid, and diclofenac salt of lidocaine prepared by the methods described in the present invention were analyzed by DSC. As shown in FIG. 1, the free base of lidocaine had an onset temperature at 66.87° C. Its endothermal maximum of melting was at 67.93° C.

Figure 2:
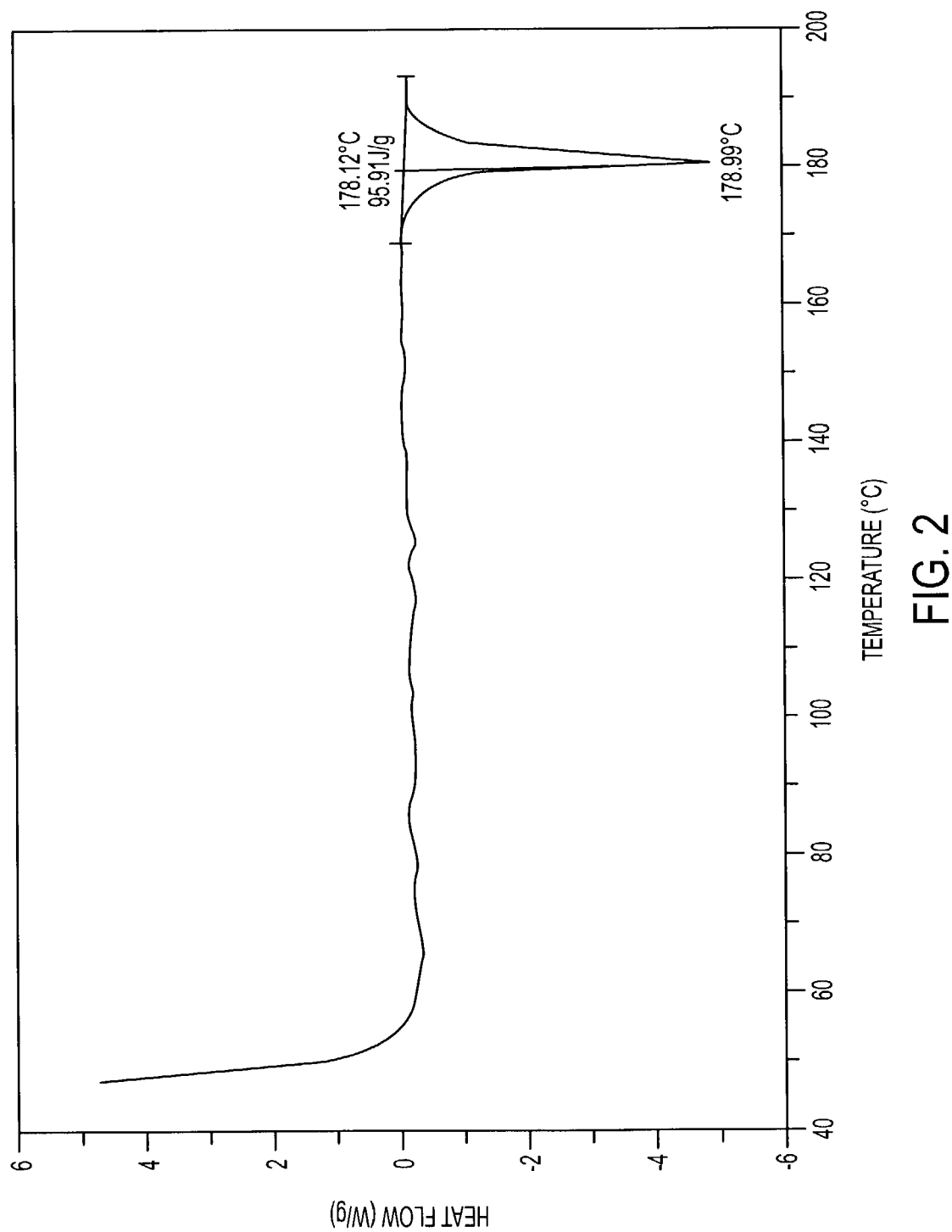
FIG. 2 shows a thermogram of differential scanning calorimetry (DSC) spectrum of free acid of diclofenac. DSC was run at a heating rate of 10° C./min. The onset temperature of the compound was at 178.12° C. The endothermal maximum of melting was at 178.99° C.

As shown in FIG. 2, the free acid of diclofenac had an onset temperature at 178.12° C. Its endothermal maximum of melting was at 178.99° C.

Figure 3:
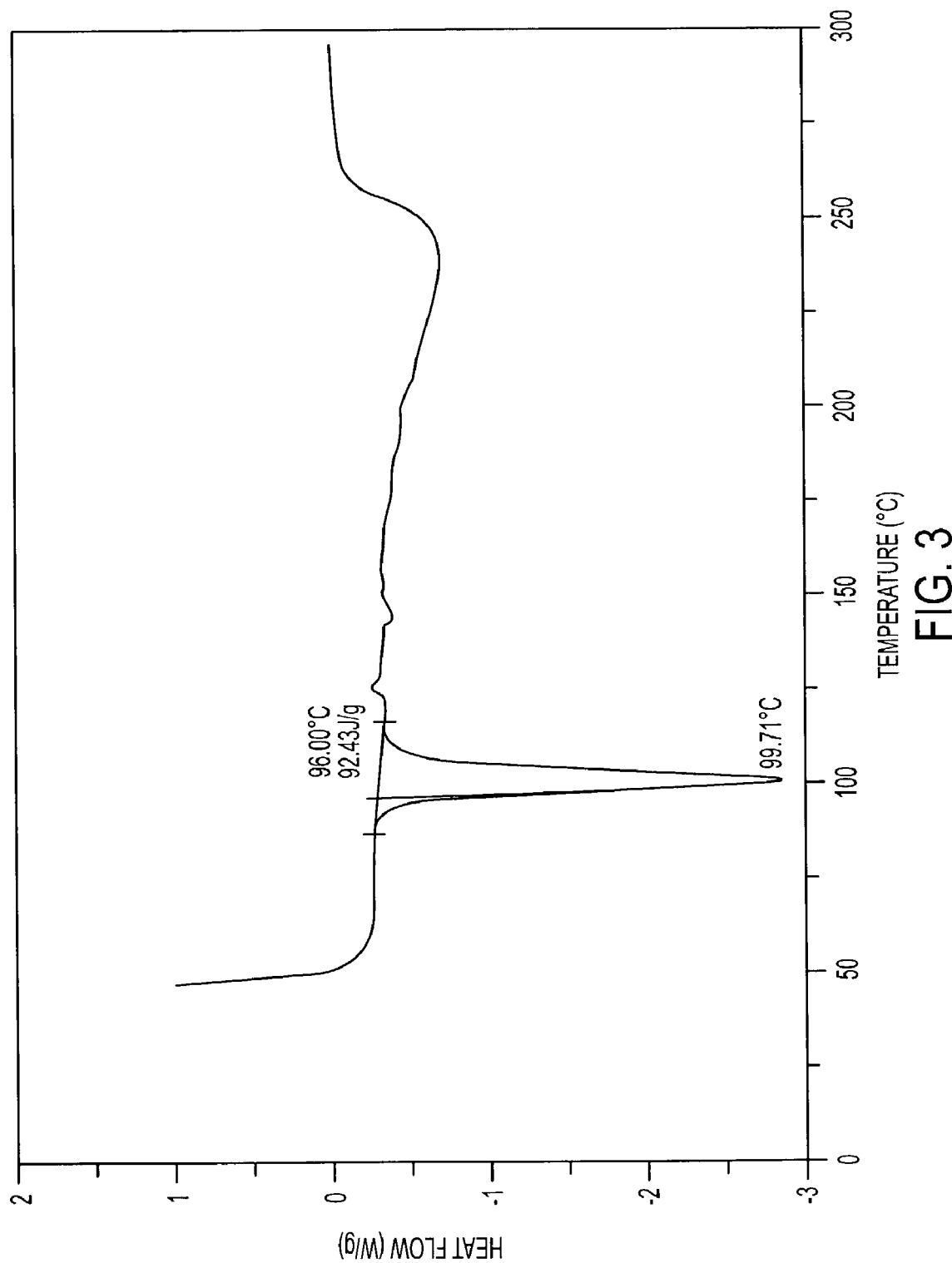
FIG. 3 shows a thermogram of differential scanning calorimetry (DSC) spectrum of a diclofenac salt of lidocaine formed by dissolving a free base of lidocaine and a free acid of diclofenac respectively in acetone before mixing together, followed by removing the solvent. The DSC was run at a heating rate of 10° C./min. The onset temperature was at 96.0° C. The endothermal maximum of melting is at 99.71° C.

The thermogram as shown in FIG. 3 represented the diclofenac salt of lidocaine prepared by the method described in Example 4 (i.e., by dissolving the lidocaine free base and diclofenac free acid in acetone followed by evaporation of the acetone). This diclofenac salt of lidocaine had an onset temperature of 96.0° C. and an endothermal maximum of melting at 99.71° C., which were significantly different from those of the lidocaine free base alone or the diclofenac free acid alone.

Figure 4:
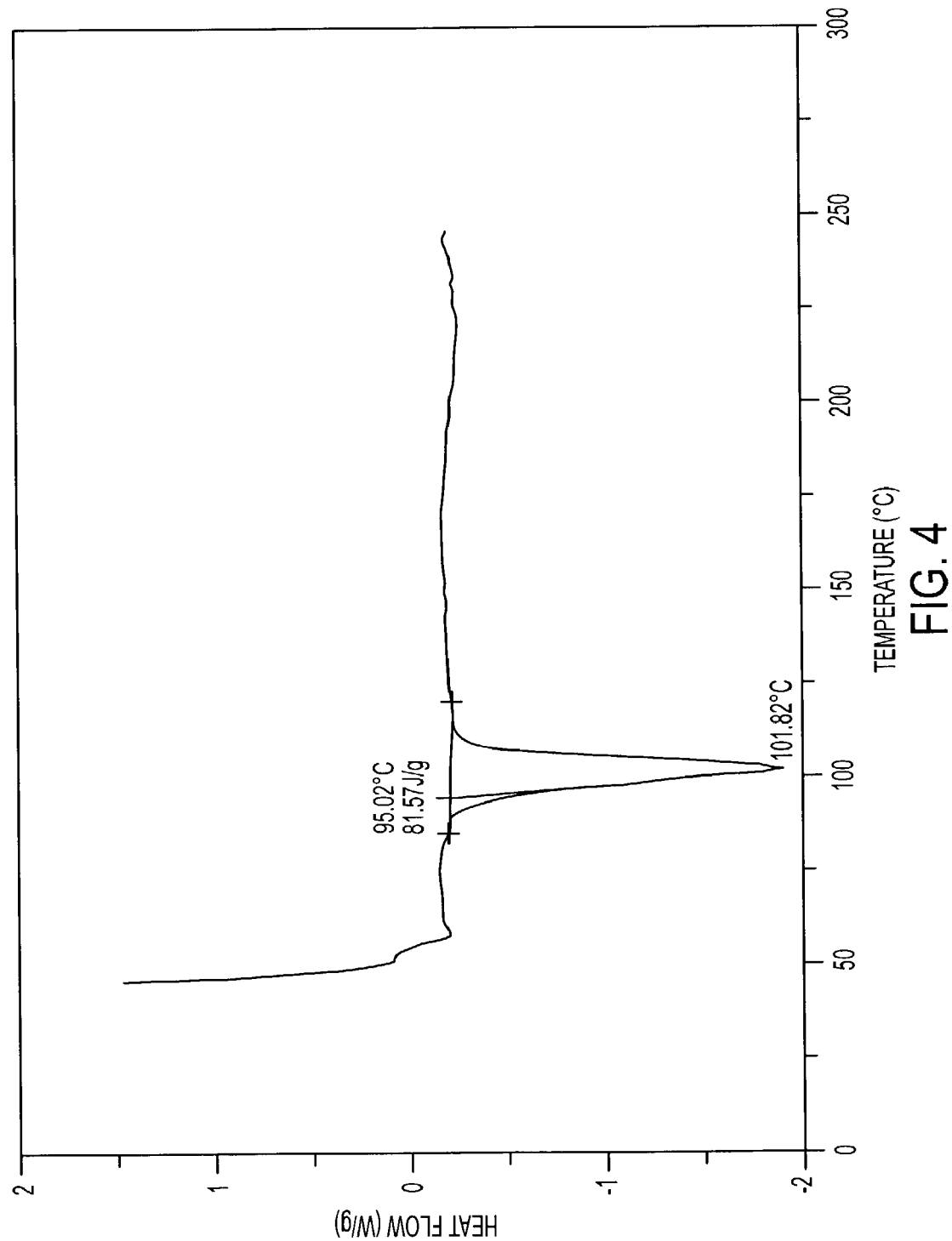
FIG. 4 shows a thermogram of differential scanning calorimetry (DSC) spectrum of a diclofenac salt of lidocaine formed by dissolving a free base of lidocaine and a free acid of diclofenac in isopropyl alcohol before mixing together, followed by removing the solvent. The DSC was run at a heating rate of 10° C./min. The onset temperature was at 95.02° C. The endothermal maximum of melting was at 101.82° C.

Also, the thermogram as shown in FIG. 4 represented the diclofenac salt of lidocaine prepared by the method described in Example 3 (i.e., by dissolving the lidocaine free base and diclofenac free acid in isopropyl alcohol followed by evaporation of the isopropyl alcohol). The diclofenac salt of lidocaine prepared by this method demonstrated an onset temperature of 95.02° C. and an endothermal maximum of melting at 101.82° C., which were similar to the onset temperature of 96.0° C. and endothermal maximum of melting at 99.71° C. shown in the diclofenac salt of lidocaine of Example 3. Also, similar to the DSC thermogram of FIG. 3, the DSC pattern of the diclofenac salt of lidocaine as shown in FIG. 4 was distinctively different from that of the lidocaine free base alone or diclofenac free acid alone.

Figure 5:
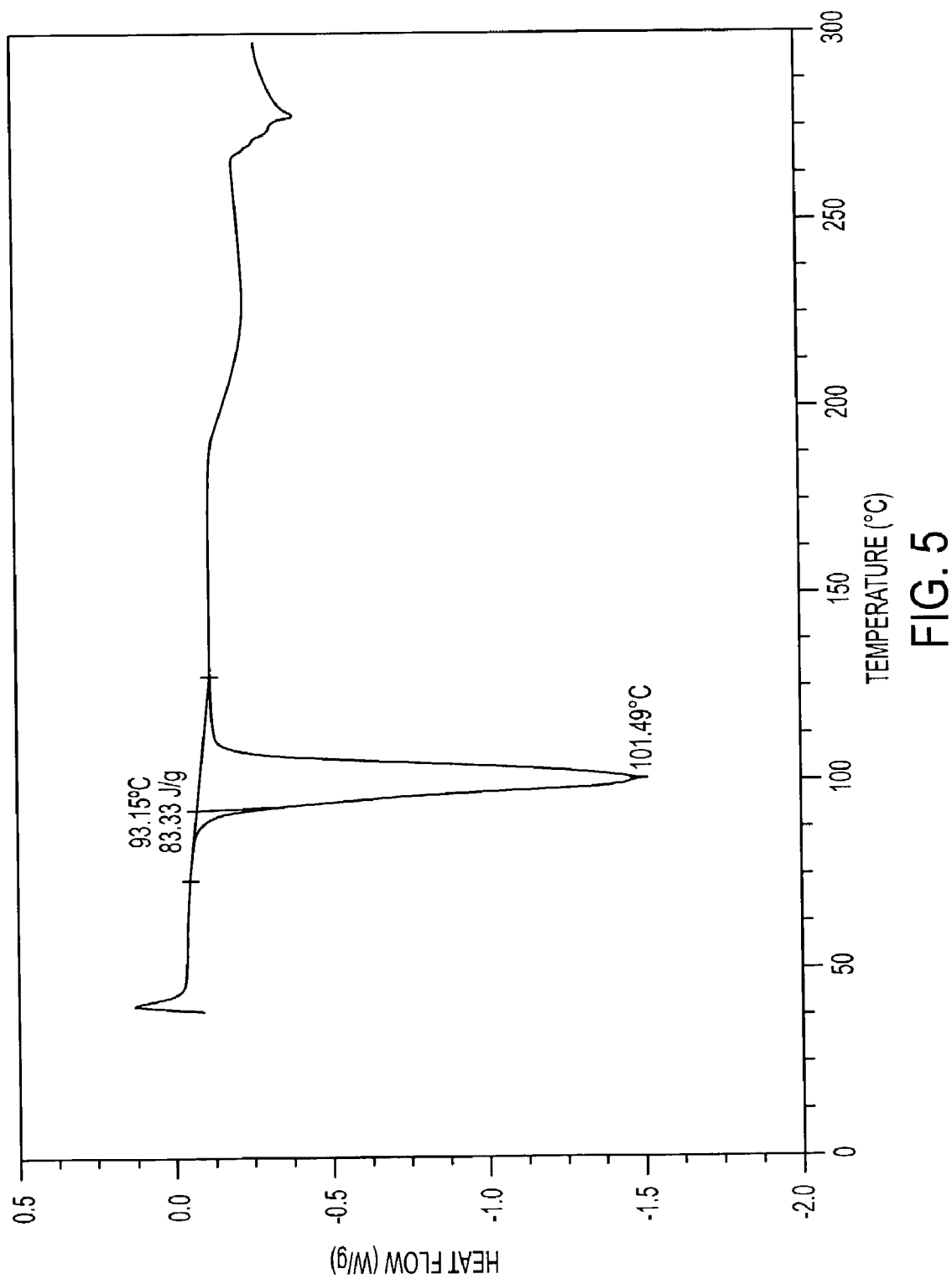
FIG. 5 shows a thermogram of differential scanning calorimetry (DSC) spectrum of a diclofenac salt of lidocaine formed by dissolving a free base of lidocaine and a free acid of diclofenac in alcohol, followed by removal of the solvent. The DSC was measured by using a heating rate of 10° C./min. The onset temperature was at 93.15° C. The endothermal maximum of melting was at 101.49° C.

Finally, as shown in FIG. 5, which represented a thermogram of DSC where the diclofenac salt of lidocaine was prepared by Example 1 (i.e., by dissolving the lidocaine free base and diclofenac free acid in alcohol followed by removing the alcohol by evaporation). This diclofenac salt of lidocaine of Example 1 showed an onset temperature of 93.16° C. and an endothermal maximum of melting at 101.49° C., which were very similar to the data shown in FIGS. 3 and 4. This finding suggested that the diclofenac salt of lidocaine prepared by different solvents demonstrated similar melting properties and were distinctively different from both the lidocaine free base alone or diclofenac free acid alone.

If the diclofenac salt of lidocaine was simply a combination of the compounds it originated, the DSC spectrum should show two separate endothermal melting peaks corresponding to the enthermal melting peaks of the lidocaine alone and the diclofenac alone. However, based on the findings in FIGS. 3–5, only one single melting peak in the DSC spectrum was found in the diclofenac salt of lidocaine. Also, the melting peak of the diclofenac salt of lidocaine ranged from (99.71° C. [FIG. 3] to 101.82° C. [FIG. 4]) was significant different from that of either the lidocaine alone [67.93° C.] or the diclofenac alone [178.99° C.]. This supported the finding that the diclofenac salt of lidocaine was not a simple mixture of the lidocaine free base and the diclofenac free acid.

EXPERIMENTAL EXAMPLE 3

Thermogravimetric (TGA) Analysis of a Diclofenac Salt of Lidocaine Made by Lidocaine Free Base-Diclofenac Free Acid Lidocaine free base, diclofenac free acid, and the diclofenac salt of lidocaine prepared by the methods described in the present invention were analyzed by TGA.

Figure 6:
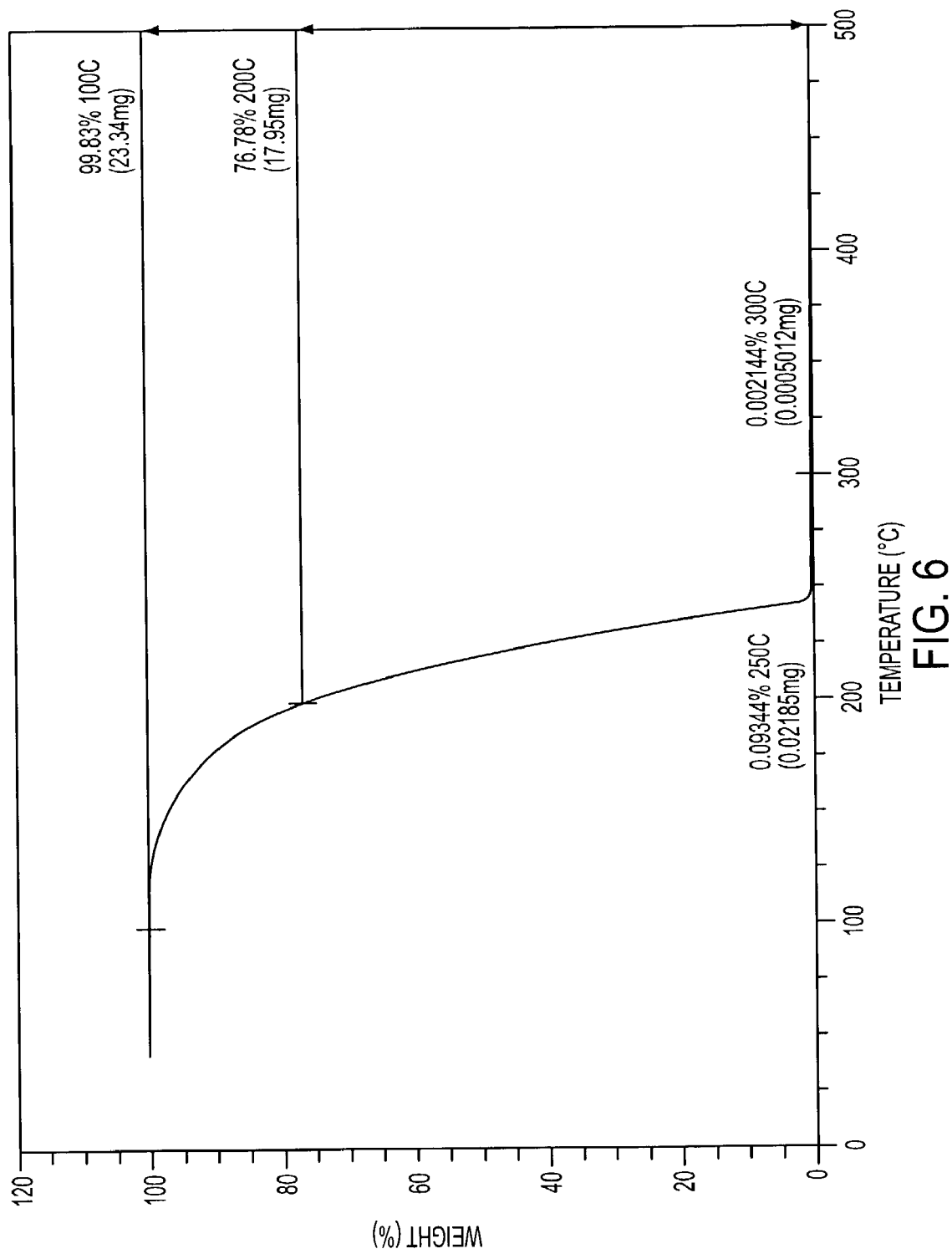
FIG. 6 shows the profile of weight loss versus temperature curve in thermo-gravimetric analysis (TGA) spectrum of a free base of lidocaine base. The TGA was run at a heating rate of 10° C./min using 2950 TGA V5.4A Universal V3.4C TA Instrument. Shown in the curve is the % of weight remained of free base lidocaine at 100° C., 200° C., 250° C., and 300° C. At 250° C., the % of weight remained was less than 0.1%.

As shown in FIG. 6, the profile of weight loss versus temperature of the free base of lidocaine base in TGA analysis showed that at 250° C., the % of the remaining weight of the free base of lidocaine was less than 0.1%.

Figure 7:
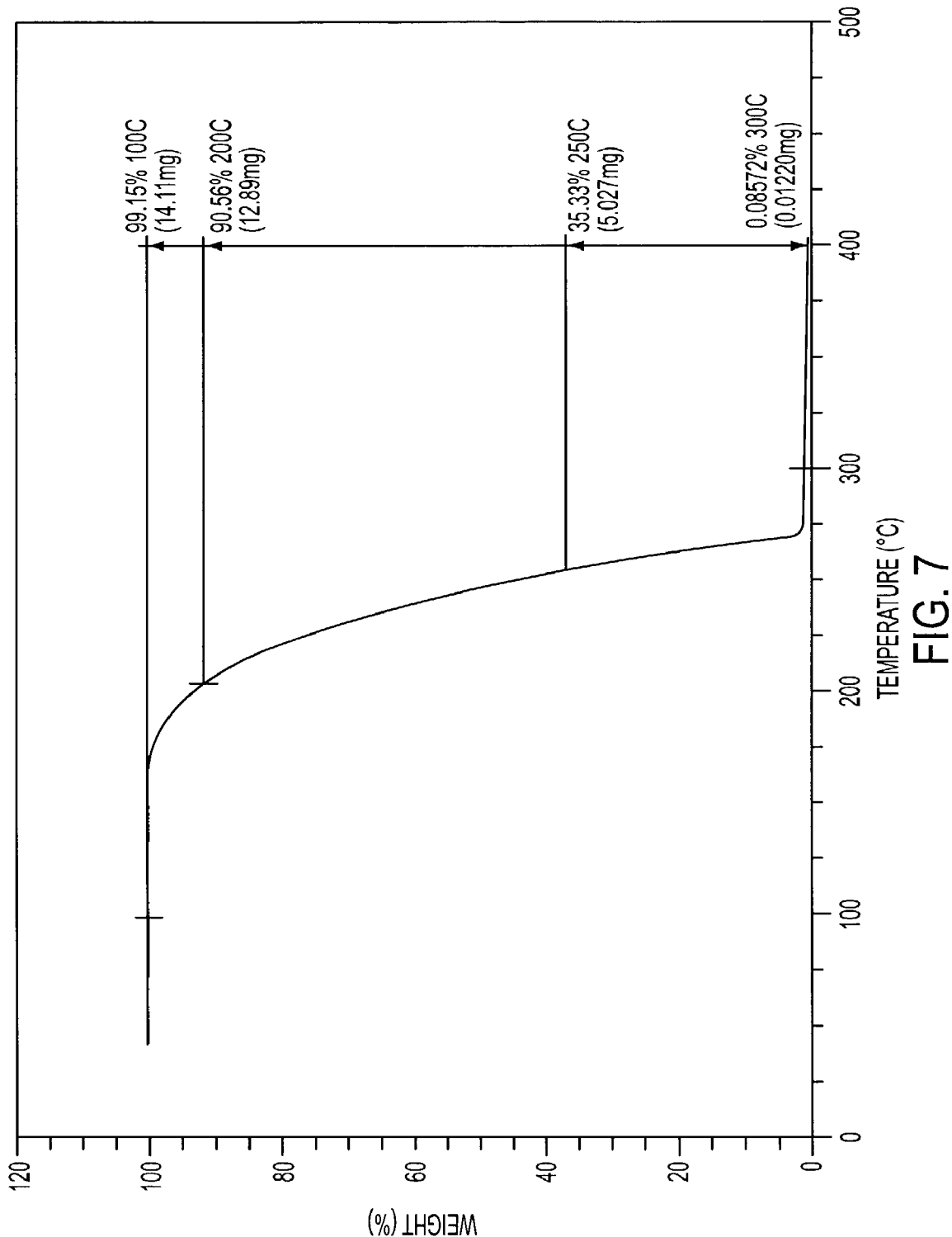
FIG. 7 shows the profile of weight loss versus temperature curve in thermogravimetric analysis (TGA) spectrum of a free acid of diclofenac acid. The TGA was run at a heating rate of 10° C./min. Shown in the curve is the % of weight remained of free base lidocaine at 100° C., 200° C., 250° C., and 300° C. At 250° C., the % of weight remained was about 35.33%.

As shown in FIG. 7, the profile of weight loss versus temperature of free acid of diclofenac in TGA analysis showed that at 250° C., the % of the remaining weight of the free acid of diclofenac was about 35.33%.

Figure 8:
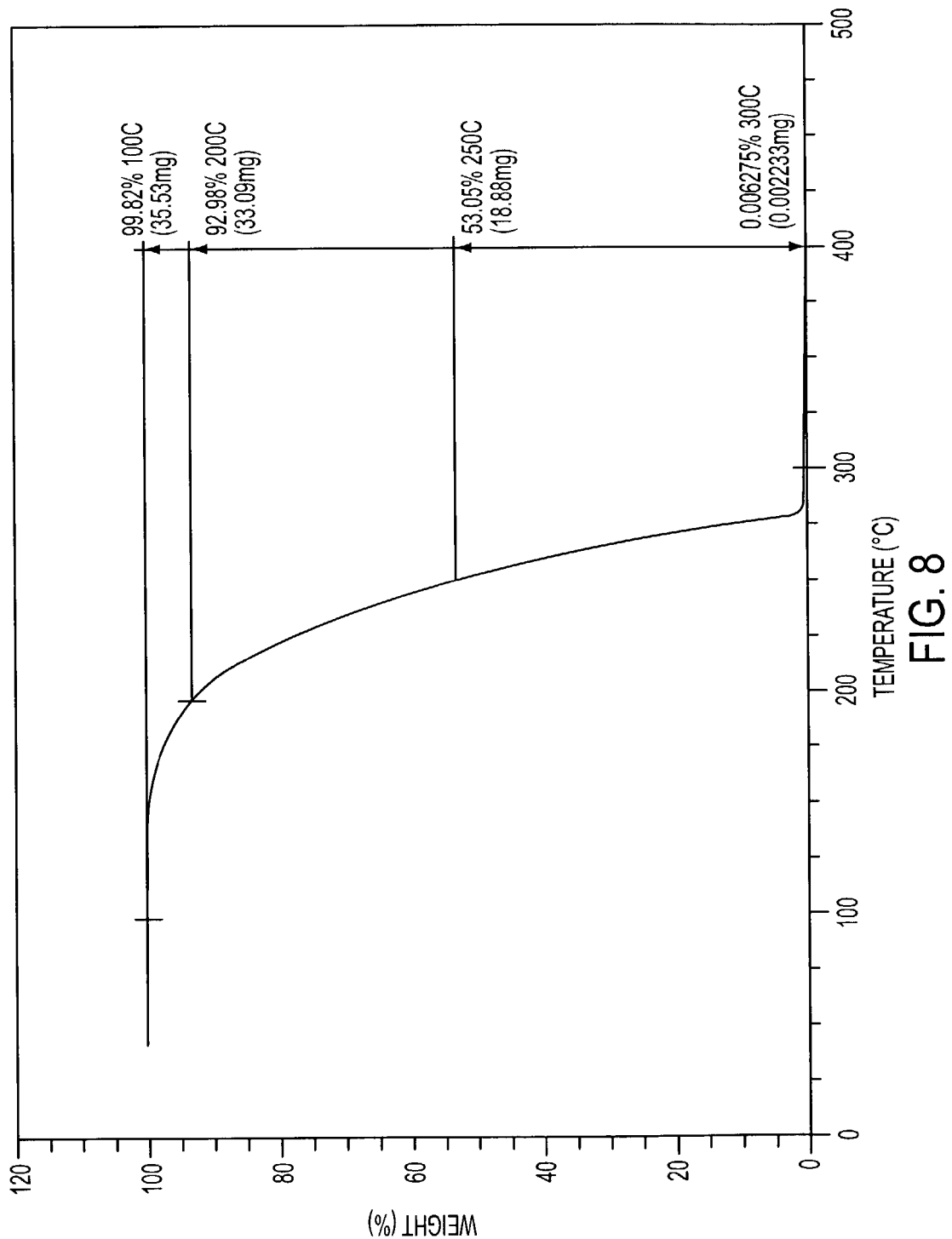
FIG. 8 shows the profile of weight loss versus temperture curve in thermo-gravimetric analysis (TGA) spectrum of a diclofenac form of lidocaine formed by dissolving a free base of lidocaine and a free acid of diclofenac respectively, in acetone before mixing together, followed by removal of the solvent using natural evaporation. The TGA was run at a heating rate of 0° C./min. Shown in the curve is the % of weight remained of the free base of lidocaine and the free acid of diclofenac at 100° C., 200° C., 250° C., and 300° C. At 250° C., the % of weight remained was about 53.05%.

However, as shown in FIG. 8, the TGA profile of weight loss versus temperature of the diclofenac salt of lidocaine showed that at 250° C., the % of the remaining weight was about 53.05%. The diclofenac salt of lidocaine was prepared by dissolving the lidocaine free base and diclofenac free acid in acetone, followed by removal of the acetone by natural evaporation.

Figure 9:
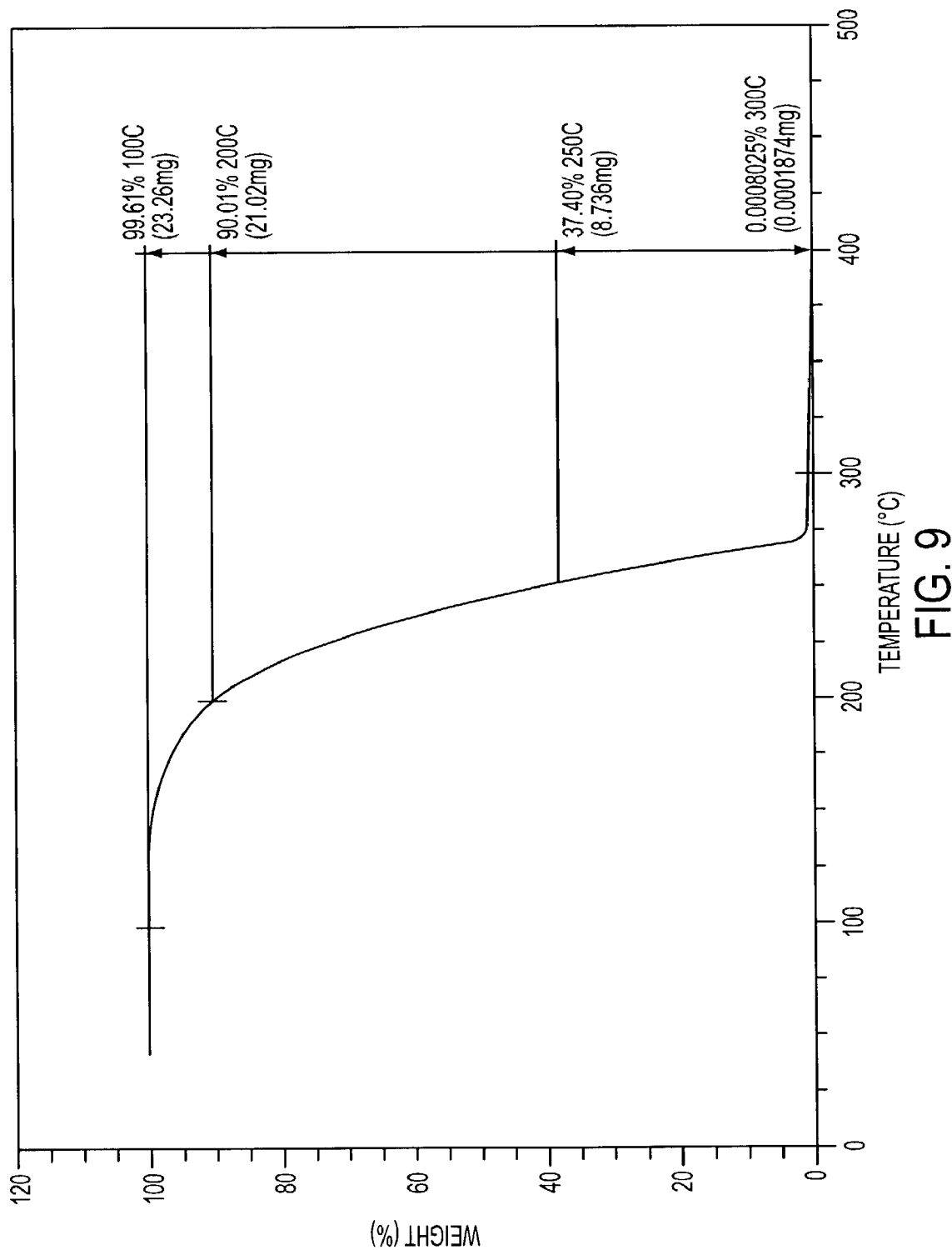
FIG. 9 shows the profile of weight loss versus temperature curve in thermo-gravimetric analysis (TGA) spectrum of a diclofenac salt of lidocaine formed by dissolving a free base of lidocaine and a free acid of diclofenac, respectively, in actone before mixing together, followed by removal of the solvent using reduced-pressure condensation. The TGA was run at a heating rate of 10° C./min. Shown in the curve is the % of weight remained of the free base of lidocaine and the free acid of diclofenac at 100° C., 200° C., 250° C., and 300° C. At 250° C., the % of weight remained was about 37.40%.

Also as shown in FIG. 9, the TGA profile of weight loss versus temperature of the diclofenac salt of lidocaine showed that at 250° C., the % of the remaining weight was about 37.40%. The diclofenac salt of lidocaine was prepared by dissolving the lidocaine free base and diclofenac free acid in acetone, followed by removal of the acetone by reduced-pressure or vacuum condensation.

The results of the TGA study indicated that the weight loss versus temperature profile of the diclofenac salt of lidocaine were distinctively different from that of the free base lidocaine but more similar to that of the free acid diclofenac. The results also indicated that different solvent removal methods might contribute to the production of the diclofenac salt of lidocaine with slightly different TGA profile.

EXPERIMENTAL EXAMPLE 4

FTIR Analysis of of a Diclofenac Salt of Lidocaine Made by Lidocaine Free Base And Diclofenac Free Acid Infrared spectroscopy (IR) has long been used in the evaluation of chemical compounds. Fourier Transform Infrared Spectroscopy (FTIR) has been used to identify and evaluate organic and inorganic materials or compounds. Using FTIR, spectral data is collected and converted from an interference pattern to a spectrum. The system provides for subtractive elimination of background spectra, such that particular chemical compounds can be identified by a molecular "fingerprint."

In the present studies, diclofenac free acid, lidocaine free base, a mixture of lidocaine free base and diclofenac free acid (without solvent dissolution or pulverization), and a diclofenac salt of lidocaine according to Example 1 (supra) were analyzed using FTIR. The results were shown in FIGS. 10–13.

Figure 10:
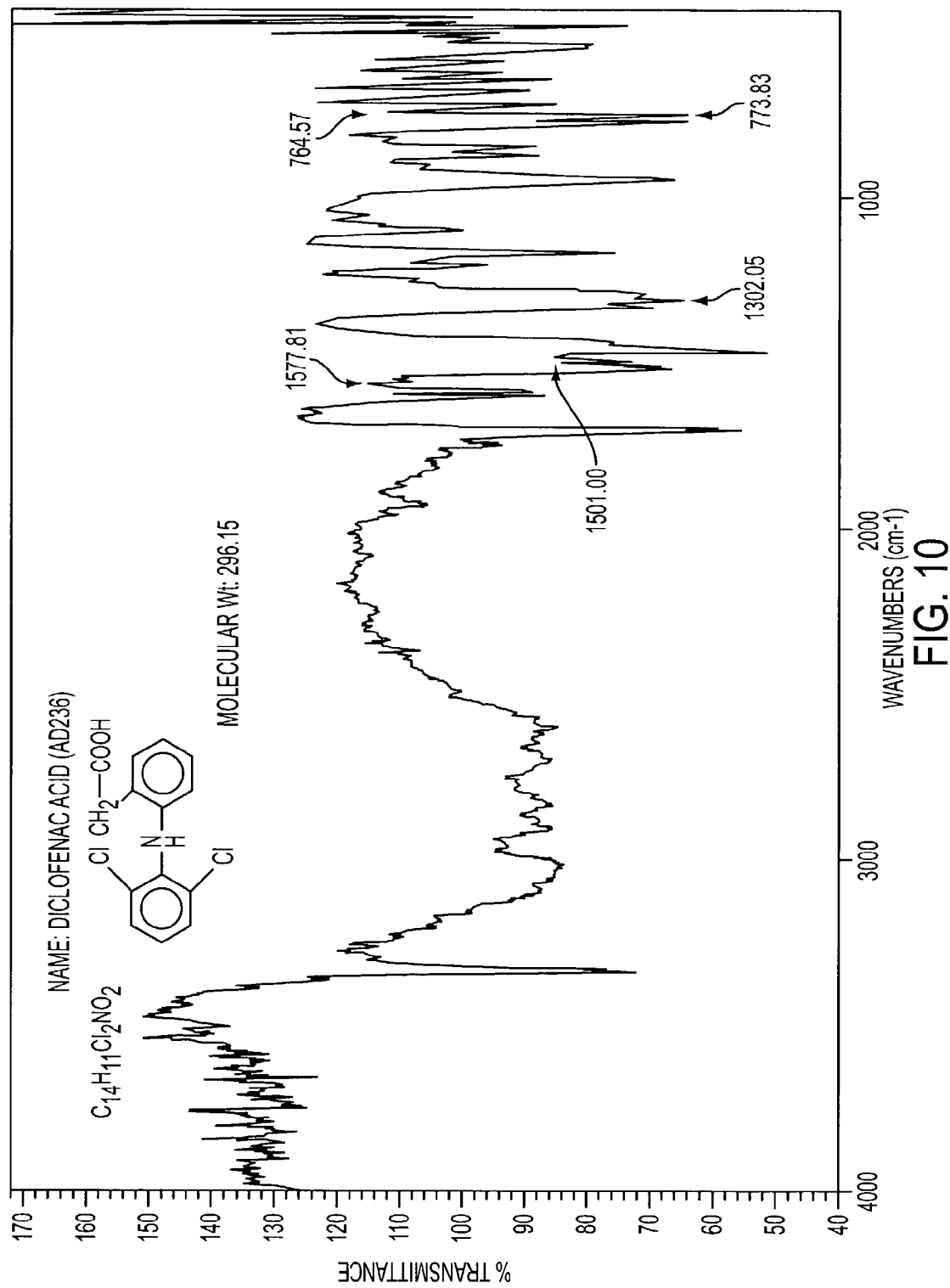
FIG. 10 shows the infra-red (IR) spectrum of diclofenac acid using Fourier-Transformed Infrared Spectroscopy (FTIR). The numbers shown on the graph depicted the peak wavelengths ($cm^{-1}$) which were unique to diclofenac free acid.

FIG. 10 shows the IR spectrum of diclofenac free acid using FTIR. There were 5 peaks identified in the diclofenac free acid IR spectrum which were unique to diclofenac. The wavelengths of these 5 peaks were 764.57 $cm^{-1}$, 773.83 $cm^{-1}$, 1302.05 $cm^{-1}$, 1501.69 $cm^{-1}$ and 1577.81 $cm^{-1}$.

Figure 11:
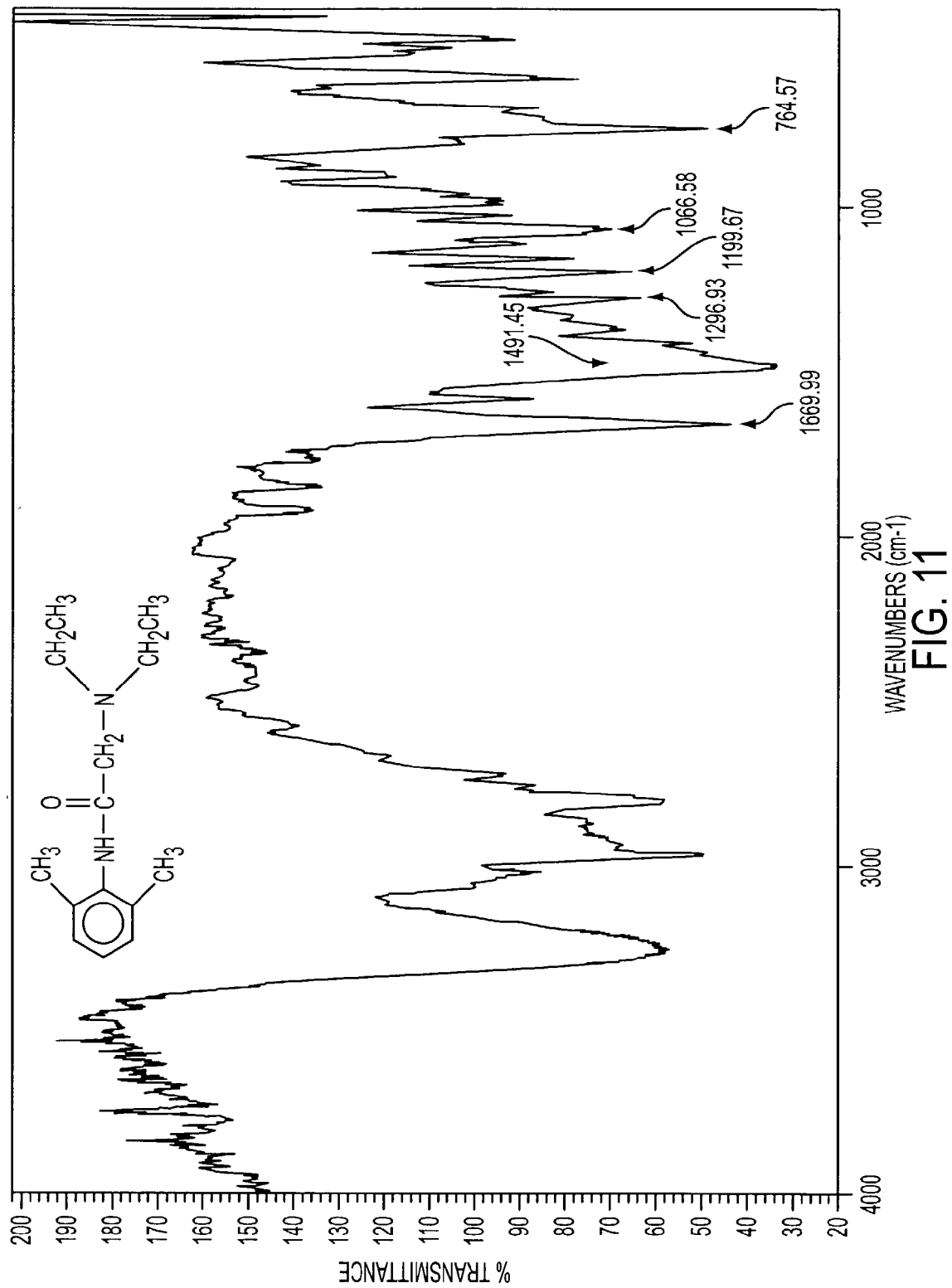
FIG. 11 shows the IR spectrum of lidocaine using FTIR. The numbers shown on the graph depicted the peak wavelengths ($cm^{-1}$) which were unique to lidocaine free base.

FIG. 11 shows the IR spectrum of lidocaine using FTIR. There were 6 peaks identified in the lidocaine free base IR spectrum which were unique to diclofenac. The wavelengths of these 6 peaks were 764.57 $cm^{-1}$, 1066.58 $cm^{-1}$, 1199.67 $cm^{-1}$, 1296.93 $cm^{-1}$, 1491.45 $cm^{-1}$, 1669.99 $cm^{-1}$. None of the peaks identified in the diclofenac free acid were identical to those found in lidocaine, suggesting that the characteristics of lidocaine and diclofenac were not common to each other.

Figure 12:
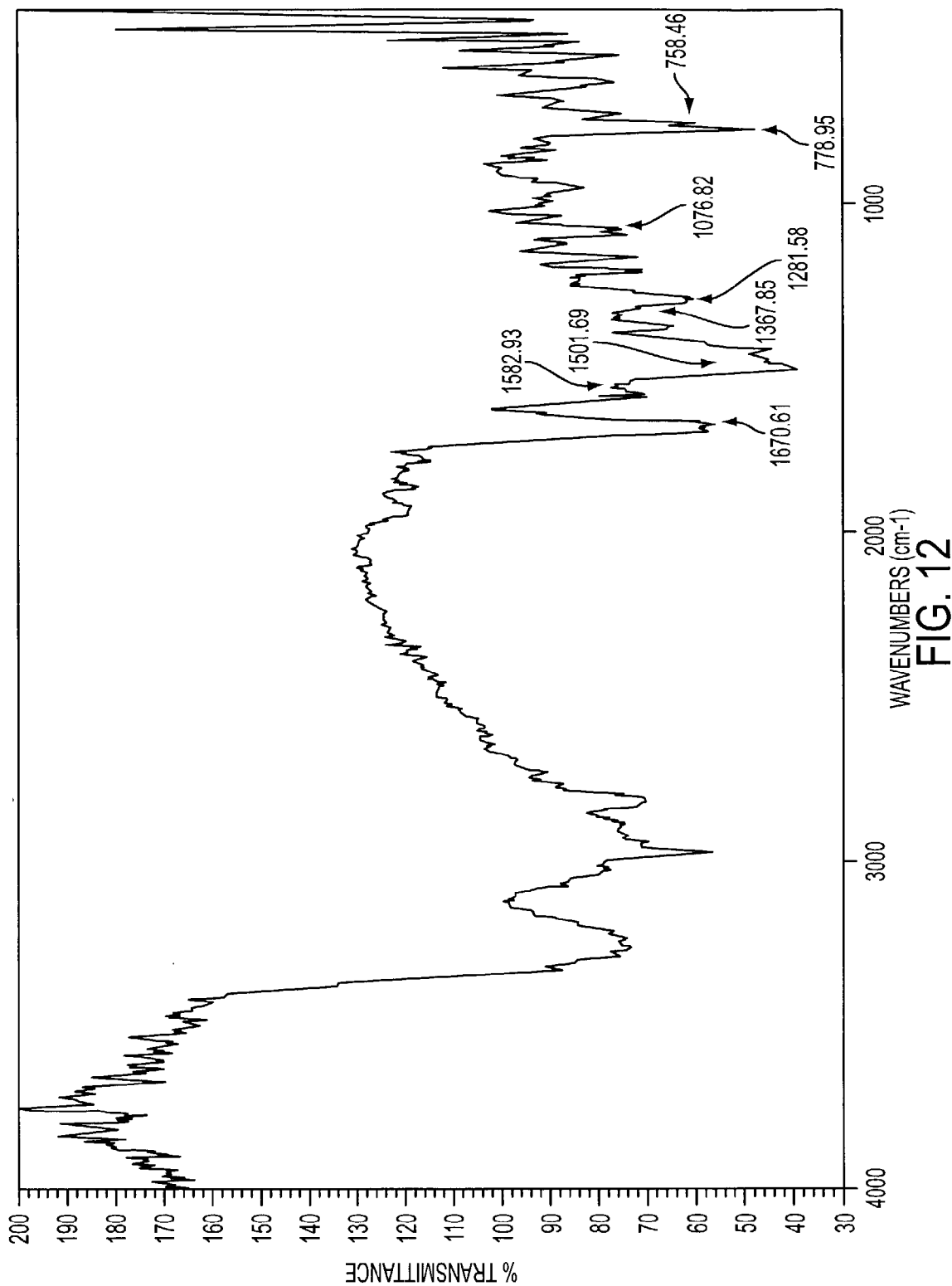
FIG. 12 shows the IR spectrum of a mixture containing equal moles of lidocaine and diclofenac acid. The mixture was neither dissolved in solvent nor pulverized. The numbers shown on the graph depicted the peak wavelengths ($cm^{-1}$) which represented the mixture of lidocaine and diclofenac.

FIG. 12 shows the IR spectrum of a mixture of equal moles of lidocaine free base and diclofenac free acid. The mixture was without further pulverization or solvent dissolution. As shown in FIG. 12, at least 8 peaks, which were 758.46 $cm^{-1}$, 778.95 $cm^{-1}$, 1076.82 $cm^{-1}$, 1281.58 $cm^{-1}$, 1367.85 $cm^{-1}$, 1501.69 $cm^{-1}$, 1582.93 $cm^{-1}$, and 1670.61 $cm^{-1}$, were found in FIG. 12. None of the peaks found in diclofenac free acid was found in the mixture of lidocaine and diclofenac was identical. There was also no identical peak between lidocaine and the mixture of lidocaine and diclofenac.

Figure 13:
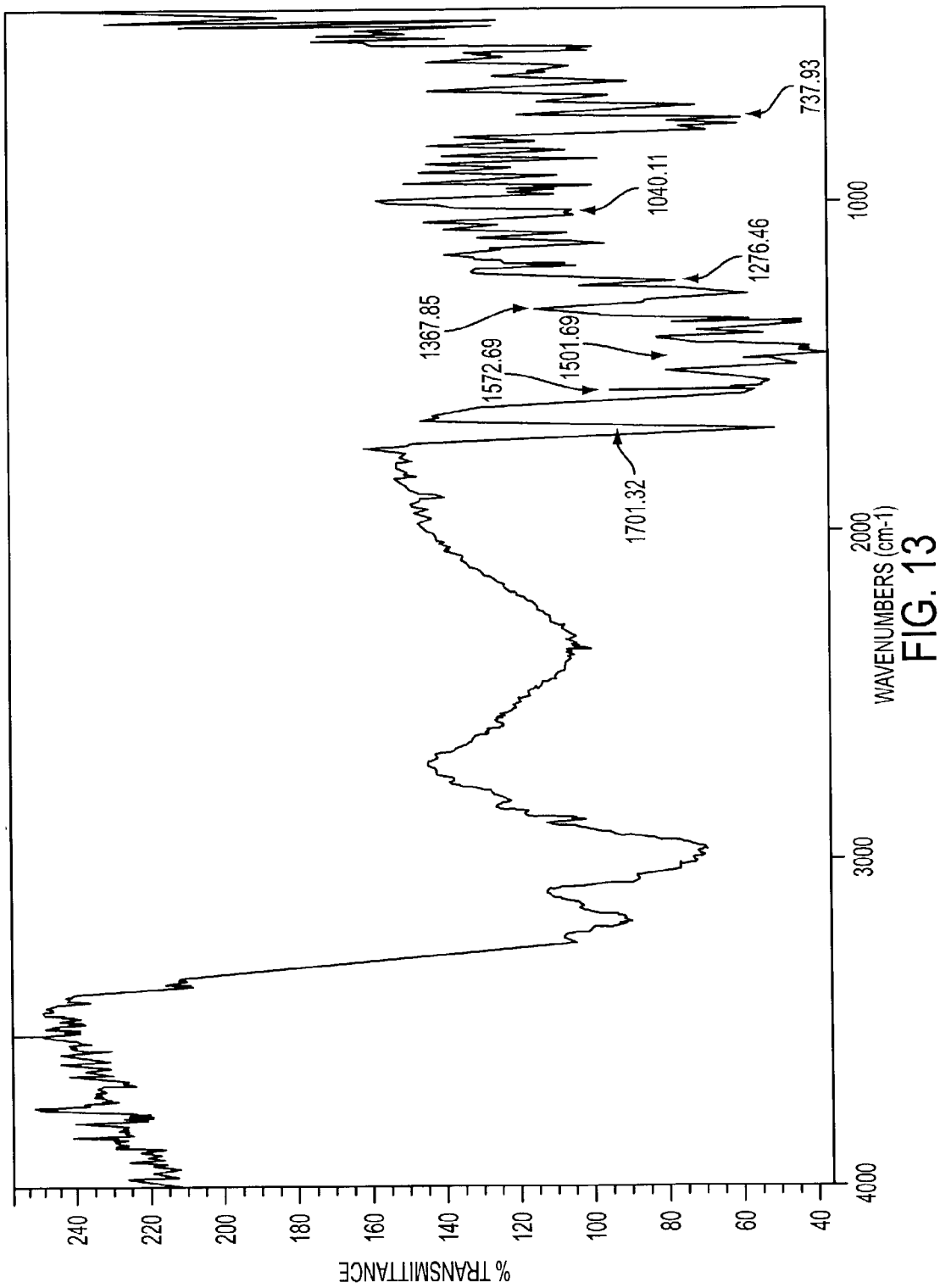
FIG. 13 shows the IR spectrum of the diclofenac salt of lidocaine which was prepared by mixing equal moles of lidocaine free base and diclofenac free acid, followed by dissolving the mixture in a solvent and then removing the solvent by vacuum condensation.

FIG. 13 shows the IR spectrum of the diclofenac salt of lidocaine prepared according to Example 1 (supra). Seven IR peaks were found in this compound, which were 737.98 $cm^{-1}$, 1041.11 $cm^{-1}$, 1276.46 $cm^{-1}$, 1367.85 $cm^{-1}$, 1501.69 $cm^{-1}$, 1572.69 $cm^{-1}$, and 1701.32 $cm^{-1}$. Only one out of the 7 peaks, i.e., 1367.85 $cm^{-1}$ was identical to the mixture of lidocaine and diclofenac (FIG. 12), suggesting that the diclofenac salt of lidocaine was chemically and physically different from the mixture of lidocaine free base and diclofenac free acid.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

What is claimed is:

1. A pharmaceutical compound which is a 1:1 salt of a non-steroidal anti-inflammatory drug (NSAID) diclofenac acid and a local anesthetic lidocaine.

2. A pharmaceutical compound which is a 1:1 salt of a non-steroidal anti-inflammatory drug (NSAID) ketorolac acid and a local anesthetic lidocaine.

3. A method for making the pharmaceutical compound according to claim 1, comprising:
   dissolving a lidocaine free base and a diclofenac free acid in a solvent to form a drug mixture;
   removing said solvent from said drug mixture to form said pharmaceutically compound.

4. The method according to claim 3, wherein said lidocaine free base and said diclofenac free acid are dissolved in said solvent respectively.

5. The method according to claim 3, wherein said lidocaine free base and said diclofenac free acid are mixed together prior to dissolution in said solvent.

6. A method for making the pharmaceutical compound according to claim 2, comprising:
   dissolving said ketorolac free acid and said lidocaine free base in a solvent to form a drug mixture; and
   removing said solvent from said drug mixture to form said pharmaceutical compound.

7. The method according to claim 3, wherein said solvent is at least one selected from the group consisting of methanol, ethanol, isopropyl alcohol, acetone, toluene, chloroform, dimethylformamide, dimethylacetamide, dimethylsulfoxide, methylene chloride and acetonitrile.

8. The method according to claim 3, wherein said solvent is removed by natural evaporation, vacuum condensation, or drying under nitrogen.

9. A method for making the pharmaceutical compound according to claim 1, comprising:
   mixing a lidocaine free base and a diclofenac free acid to form a drug mixture;
   pulverizing said drug mixture by a physical-mechanical means to form said pharmaceutical compound.

10. A method for making the pharmaceutical compound according to claim 2, comprising:
    mixing said ketorolac free acid and said lidocaine free base to form a drug mixture;
    pulverizing said drug mixture by a physical-mechanical means to form said pharmaceutical compound.

11. A pharmaceutical formulation comprising the pharmaceutical compound of claim 1 and a pharmaceutically acceptable carrier.

12. The pharmaceutical formulation according to claim 11, wherein said pharmaceutical formulation is for topical treatment.

13. The pharmaceutical formulation according to claim 12, wherein said pharmaceutical formulation for topical treatment is in the form of solution, gel, emugel, cream, ointment, lotion, transdermal patch, or eye drop.

14. The pharmaceutical formulation according to claim 11, wherein said pharmaceutical formulation is for parenteral injection.

15. A method for treating patients with localized pain comprising topically treating said patients with an effective amount of the pharmaceutical formulation according to claim 12.

16. The method according to claim 15, wherein said localized pain is muscle pain, joint pain, pain associated with herpes infection, and wound pain.

17. A method for treating patients with localized pain comprising parenterally administering an effective amount of the pharmaceutical formulation according to claim 11.

18. The method according to claim 17, wherein said localized pain is muscle pain, joint pain, pain associated with herpes infection, and wound pain.

19. The pharmaceutical compound of claim 1, wherein pharmaceutical compound exhibits combined therapeutic effects of local anesthetic and anti-inflammatory activities.

20. The pharmaceutical compound of claim 1, wherein said pharmaceutical compound is prepared by dissolving said lidocaine free base and said diclofenac free acid in a solvent to form a drug mixture; and removing said solvent from said drug mixture to form said pharmaceutically compound.

21. The pharmaceutical compound of claim 1, wherein said pharmaceutical compound is prepared by mixing said lidocaine free base and said diclofenac free acid to form a drug mixture;

pulverizing said drug mixture by a physical-mechanical means to form said solid pharmaceutical compound.

22. The pharmaceutical compound of claim 1, wherein said pharmaceutical compound is formed without solvent.

23. The pharmaceutical compound of claim 2, wherein said pharmaceutical compound is prepared by dissolving said lidocaine free base and said ketorolac free acid in a solvent to form a drug mixture; and removing said solvent from said drug mixture to form said pharmaceutically compound.

24. The pharmaceutical compound of claim 2, wherein said pharmaceutical compound is prepared by mixing said lidocaine free base and said ketorolac free acid to form a drug mixture;

pulverizing said drug mixture by a physical-mechanical means to form said pharmaceutical compound.

25. The pharmaceutical compound of claim 2, wherein said pharmaceutical compound is formed without solvent.

26. The pharmaceutical compound of claim 22, wherein said pharmaceutical compound has an endothermal maximum of melting above 90° C. in differential scanning calorimetry analysis.

\* \* \* \* \*

UNITED STATES PATENT AND TRADEMARK OFFICE
CERTIFICATE OF CORRECTION

PATENT NO. : 7,166,641 B2  
APPLICATION NO. : 10/262098  
DATED : January 23, 2007  
INVENTOR(S) : Fang-Yu Lee et al.

It is certified that error appears in the above-identified patent and that said Letters Patent is hereby corrected as shown below:

Column 5, line 13, delete "meas", and insert --means--.

Column 6, line 34, delete "0°C./min", and insert --10°C./min--.

Column 6, line 42, delete "actone", and insert --acetone--.

Column 10, line 40, delete "mixed", and insert --mix--.

Column 10, line 44, delete "derivtives", and insert --derivatives--.

Column 11, line 16, delete "alchohol", and insert --alcohol--.

Column 11, line 27, delete "as", and insert --by--.

Column 11, line 33, delete "BV", and insert --by--.

Column 12, line 25, delete "nature", and insert --natural--.

Column 12, line 33, delete "seqentially", and insert --sequentially--.

Column 13, line 27, delete "Method 1", and insert --Method 1:--.

Column 16, line 54, delete "Method: 1", and insert --Method 1:--.

Column 16, line 63, delete "Method: 2", and insert --Method 2:--.

Column 17, line 23, delete "Method: 1", and insert --Method 1:--.

Column 17, line 33, delete "Method: 2", and insert --Method 2:--.

Column 17, line 61, delete "Method: 1", and insert --Method 1:--.

Column 18, line 5, delete "Method: 2", and insert --Method 2:--.

Column 18, line 32, delete "Method: 1", and insert --Method 1:--.

UNITED STATES PATENT AND TRADEMARK OFFICE
CERTIFICATE OF CORRECTION

PATENT NO. : 7,166,641 B2
APPLICATION NO. : 10/262098
DATED : January 23, 2007
INVENTOR(S) : Fang-Yu Lee et al.

It is certified that error appears in the above-identified patent and that said Letters Patent is hereby corrected as shown below:

Column 18, line 42, delete "Method: 2", and insert --Method 2:--.

Column 18, line 60, delete "ingredients", and insert --ingredients:--.

Column 19, line 8, delete "sodium", and insert --Sodium--.

Column 22, line 40, delete "enthermal", and insert --endothermal--.

Column 23, line 28, delete "of of", and insert --of--.

Signed and Sealed this

Twenty-third Day of June, 2009

JOHN DOLL
*Acting Director of the United States Patent and Trademark Office*